(12) United States Patent
Kinney et al.

(10) Patent No.: US 7,365,242 B2
(45) Date of Patent: Apr. 29, 2008

(54) SUPPRESSION OF SPECIFIC CLASSES OF SOYBEAN SEED PROTEIN GENES

(75) Inventors: Anthony J. Kinney, Wilmington, DE (US); Gary M. Fader, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 333 days.

(21) Appl. No.: 10/757,155

(22) Filed: Jan. 14, 2004

(65) Prior Publication Data

US 2004/0139503 A1 Jul. 15, 2004

Related U.S. Application Data

(62) Division of application No. 09/758,652, filed on Jan. 11, 2001, now Pat. No. 6,703,544, which is a division of application No. 09/108,010, filed on Jun. 30, 1998, now Pat. No. 6,362,399.

(60) Provisional application No. 60/019,940, filed on Jun. 14, 1996.

(51) Int. Cl.
*A01H 5/00* (2006.01)
*C12N 15/82* (2006.01)
*A23K 1/00* (2006.01)

(52) U.S. Cl. .................. 800/312; 435/415; 435/419; 426/635

(58) Field of Classification Search .................. None
See application file for complete search history.

(56) References Cited

U.S. PATENT DOCUMENTS 5,936,140 A * 8/1999 Beach .................. 800/312

FOREIGN PATENT DOCUMENTS

| EP | 0 591 530 A1 | 4/1994 |
|---|---|---|
| EP | 0 620 281 A2 | 10/1994 |
| WO | 94/11516 | 5/1994 |
| WO | 95/27068 | 10/1995 |

OTHER PUBLICATIONS

Michael A. Lawton et. al., Expression of a Soybean B-Conclycinin Gene Under the Control of the Cauliflower Mosaic Virus 35S and 19S Promoters in Transformed Petunia Tissues, Plant Molecular Biology, 1987, vol. 9:315-324.

T. Ogawa et al., Genetic improvement of seed storage proteins using three variant alleles of 7S globulin subunits in soybean (*Glycine max L.*), Chemical Abstracts, 111, No. 23, Abstract No. 212128, 1989.

K. Takahashi, et al., An induced mutant line lacking the α-subunit of β-conglycinin soybean (*Glycine max (L.)* Merrill), Biological Abstracts, 98, Abstract No. 83825, 1994.

K. Yagasaki et al., Inheritance of glycinin subunits and characterization of glycinin molecules lacking the subunits in soybean (*Glycine max (L.)* Merr.), Biological Abstracts, 101, Abstract No. 137658, 1996.

Kirin Brewery KK, Recombination Plasmid Obtain Recombination Gene Plasmid Plant, WPI/Derwent, AN 90-228488, PN JP2156889 A, Jun. 1990.

R. N. Beachy et al., Accumulation and assembly of soybean β-conglycinin in seeds of transformed petunia plants, Embo Journal, 4, 1985, 3047-3053.

S. Utsumi et al., Synthesis, processing and accumulation of modified glycinins of soybean in the seeds, leaves and stems of transgenic tobacco, Plant Science, 92, 191-202, 1993.

Y. -D. Park et al., Gene silencing mediated by promoter homology occurs at the level of transcription and results in meiotically heritable alterations in methylation and gene activity, The Plant Journal, 9, No. 2, 183-194, 1996.

J. A. Brusslan, et al., Isolation of new promoter-mediated co-suppressed lines in *Arabidopsis thaliana*, Plant Molecular Biology, 27, 809-813, 1995.

E. P. Heppard, Developmental and Growth Temperature Regulation of Two Different Microsomal ω-6 Desaturase Genes in Soybeans, Plant Physiol., 110, 311-319, 1996.

\* cited by examiner

Primary Examiner—Elizabeth F. McElwain

(57) ABSTRACT

This invention concerns the construction of transgenic soybean lines wherein the expression of genes encoding seed storage proteins are modulated to effect a change in seed storage protein profile of transgenic plants. Modification of the seed storage protein profile can result in the production of novel soy protein products with unique and valuable functional characteristics.

1 Claim, 9 Drawing Sheets

SUPPRESSION OF SPECIFIC CLASSES OF SOYBEAN SEED PROTEIN GENES

This case is a divisional application under 37 CFR § 1.53(b). Specifically, this application is a divisional of application Ser. No. 09/758,652 filed Jan. 11, 2001 now U.S. Pat. No. 6,703,544 which was a divisional application of application Ser. No. 09/108,010 filed Jun. 30, 1998 now U.S. Pat. No. 6,362,399 which claimed the benefit of provisional application No. 60/019,940 filed Jun. 14, 1996, the entire contents of which are hereby incorporated by reference.

FIELD OF THE INVENTION

This invention concerns the construction of transgenic soybean lines wherein the expression of genes encoding seed storage proteins is modified to effect a change in seed storage protein profile of transgenic plants. Such modified transgenic soybean lines are used for the production of novel soy protein products with unique and valuable functional characteristics.

BACKGROUND OF THE INVENTION

Soybean seeds contain from 35% to 55% protein on a dry weight basis. The majority of this protein is storage protein, which is hydrolyzed during germination to provide energy and metabolic intermediates needed by the developing seedling. The soybean seed's storage protein is an important nutritional source when harvested and utilized as a livestock feed. In addition, it is now generally recognized that soybeans are the most economical source of protein for human consumption. Soy protein or protein isolates are already used extensively for food products in different parts of the world. Much effort has been devoted to improving the quantity and quality of the storage protein in soybean seeds.

The seeds of most plant species contain what are known in the art as seed storage proteins. These have been classified on the basis of their size and solubility (Higgins, T. J. (1984) *Ann. Rev. Plant Physiol.* 35:191-221). While not every class is found in every species, the seeds of most plant species contain proteins from more than one class. Proteins within a particular solubility or size class are generally more structurally related to members of the same class in other species than to members of a different class within the same species. In many species, the seed proteins of a given class are often encoded by multigene families, sometimes of such complexity that the families can be divided into subclasses based on sequence homology.

There are two major soybean seed storage proteins: glycinin (also known as the 11S globulins) and β-conglycinin (also known as the 7S globulins). Together, they comprise 70 to 80% of the seed's total protein, or 25 to 35% of the seed's dry weight. Glycinin is a large protein with a molecular weight of about 360 kDa. It is a hexamer composed of the various combinations of five major isoforms (commonly called subunits) identified as G1, G2, G3, G4 and G5. Each subunit is in turn composed of one acidic and one basic polypeptide held together by a disulfide bond. Both the acidic and basic polypeptides of a single subunit are coded for by a single gene. Hence, there are five non-allelic genes that code for the five glycinin subunits. These genes are designated Gy1, Gy2, Gy3, Gy4 and Gy5, corresponding to subunits G1, G2, G3, G4 and G5, respectively (Nielsen, N. C. et al. (1989) *Plant Cell* 1:313-328).

Genomic clones and cDNA's for glycinin subunit genes have been sequenced and fall into two groups based on nucleotide and amino acid sequence similarity. Group I consists of Gy1, Gy2, and Gy3, whereas Group II consists of Gy4 and Gy5. There is greater than 85% similarity between genes within a group (i.e., at least 85% of the nucleotides of Gy1, Gy2 and Gy3 are identical, and at least 85% of the nucleotides of Gy4 and Gy5 are identical), but only 42% to 46% similarity between the genes of Group I and Group II.

β-Conglycinin (a 7S globulin) is a heterogeneous glycoprotein with a molecular weight ranging from 150 and 240 kDa. It is composed of varying combinations of three highly negatively charged subunits identified as α, α' and β. cDNA clones representing the coding regions of the genes encoding the the α and α' subunits have been sequenced and are of similar size; sequence identity is limited to 85%. The sequence of the cDNA representing the coding region of the β subunit, however, is nearly 0.5 kb smaller than the α and α' cDNAs. Excluding this deletion, sequence identity to the α and α' subunits is 75-80%. The three classes of β-conglycinin subunits are encoded by a total of 15 subunit genes clustered in several regions within the genome soybean (Harada, J. J. et al. (1989) *Plant Cell* 1:415-425).

New soy based products such as protein concentrates, isolates, and textured protein products are increasingly utilized in countries that do not necessarily accept traditional oriental soy based foods. Use of these new products in food applications, however, depends on local tastes and functional characteristic of the protein products relative to recipe requirements. Over the past 10 years, significant effort has been aimed at understanding the functional characteristics of soybean proteins. Examples of functional characteristics include water sorption parameters, wettability, swelling, water holding, solubility, thickening, viscosity, coagulation, gelation characteristics and emulsification properties. A large portion of this body of research has focused on study of the β-conglycinin and glycinin proteins individually, as well as how each of these proteins influences the soy protein system as a whole (Kinsella, J. E. et al. (1985) *New Protein Foods* 5:107-179; Morr, C. V. (1987) *JAOCS* 67:265-271; Peng, L. C. et al. (1984) *Cereal Chem* 61:480-489). Because functional properties are directly related to physiochemical properties of proteins, the structural differences of β-conglycinin and glycinin result in these two proteins having significantly different functional characteristics. Differences in thermal aggregation, emulsifying properties, and water holding capacity have been reported. In addition, gelling properties vary as well, with glycinin forming gels that have greater tensile strain, stress, and shear strength, better solvent holding capacity, and lower turbidity. However, soy protein products produced today are a blend of both glycinin and β-conglycinin and therefore have functional characteristics dependent on the blend of glycinin's and β-conglycinin's individual characteristics. For example, when glycinin is heated to 100° C., about 50% of the protein is rapidly converted into soluble aggregates. Further heating results in the enlargement of the aggregates and in their precipitation. The precipitate consists of the glycinin's basic polypeptides; the acidic polypeptides remain soluble. The presence of β-conglycinin inhibits the precipitation of the basic polypeptides by forming soluble complexes with them. Whether heat denaturation is desireable or not depends on the intended use. If one could produce soy protein products containing just one or the other storage protein, products requiring specific physical characteristics derived from particular soy proteins would become available or would be more economical to produce.

Over the past 20 years, soybean lines lacking one or more of the various storage protein subunits (null mutations) have been identified in the soybean germplasm or produced using mutational breeding techniques. Breeding efforts to combine mutational events have resulted in soybean lines whose seeds contain about half the normal amount of β-conglycinin (Takashashi, K. et al. (1994) *Breeding Science* 44:65-66; Kitamura, J. (1995) *JARQ* 29:1-8). The reduction of β-conglycinin is controlled by three independent recessive mutations. Recombining glycinin subunit null mutations have resulted in lines whose seeds have significantly reduced amounts of glycinin (Kitamura, J. (1995) *JARQ* 29:1-8). Again, reduction is controlled by three independent recessive mutations. Developing agronomically viable soybean varieties from the above lines, in which the seed contains only glycinin or β-conglycinin, will be time consuming and costly. Each cross will result in the independent segregation of the three mutational events. In addition, each mutational event will need to be in the homozygous state. Development of high yielding agronomically superior soybean lines will require the screening and analysis of a large number of progeny over numerous generations.

Antisense technology has been used to reduce specific storage proteins in seeds. In *Brassica napus*, napin (a 2S albumin) and cruciferin (an 11S globulin) are the two major storage proteins, comprising about 25% and 60% of the total seeds protein, respectively. Napin proteins are coded for by a large multi-gene family of up to 16 genes; several cDNA and genomic clones have been sequenced (Josefsson, L.-G. et al. (1987) *J. Biol Chem* 262:12196-12201; Schofield, S. and Crouch, M. L. (1987) *J. Biol. Chem.* 262:12202-12208). The genes exhibit greater than 90% sequence identity in both their coding and flanking regions. The cruciferin gene family is equally complex, comprising 3 subfamilies with a total of 8 genes (Rodin, J. et al. (1992) *Plant Mol. Biol.* 20:559-563). Kohno-Murase et al. ((1994) *Plant Mol. Biol.* 26:1115-1124) demonstrated that a napin antisense gene using the napA gene driven by the napA promoter could be used to construct transgenic plants whose seeds contained little or no napin.

The same group (Kohno-Murase et al. (1995) *Theoret. Applied Genetics* 91:627-631) attempted to reduce cruciferin (11S globulin) expression in *Brassica napus* by expressing an antisense form of a cruciferin gene (cruA, encoding an alpha 2/3 isoform) under the control of the napA promoter. In this case the results were more complex. The cruciferins are divided into three subclasses based on sequence identity (alpha 1, 2/3, and 4); the classes each have from 60-75% sequence identity with each other (Rodin, J. et al. (1992) *Plant Mol. Biol.* 20:559-563). Expression of the antisense gene encoding the alpha 2/3 isoform resulted in lower levels of the alpha 1 and 2/3 forms. However, there was no reduction in the expression of the alpha 4 class.

Antisense technology was used to reduce the level of the seed storage protein, glutelin, in rice. Expression of the seed specific glutelin promoter operably linked to the full length antisense glutelin coding region resulted in about a 25% reduction in glutelin protein levels (U.S. Pat. No. 5,516,668).

SUMMARY OF THE INVENTION

The instant invention provides a method for reducing the quantity glycinin or β-conglycinin (11S or 7S globulins, respectively) seed storage proteins in soybeans. In one embodiment, cosuppression technology was used to suppress the expression of genes encoding the 7S-globulin class of seed protein genes. Genes encoding either two (α and α') or all three subclasses (α, α' and β) of 7S globulins were suppressed by expression of the gene encoding a single subclass (α) of β-conglycinin, resulting in soybean lines with altered seed storage profiles. In another embodiment, a method for supressing two completely different genes, only one of which is a seed protein gene, is presented, allowing for multiple changes in seed composition. Surprisingly, expression of a chimeric gene comprising the promoter region of a soybean seed storage protein operably linked to the coding region of a soybean gene whose expression alters the fatty acid profile of transgenic soybean seeds resulted in simultaneous alteration of two distinct phenotypic traits: seed storage protein profile and seed oil profile.

The method for reducing the quantity of soybean seed storage protein taught herein comprises the following steps:

(a) constructing a chimeric gene comprising (i) a nucleic acid fragment encoding a promoter that is functional in the cells of soybean seeds, (ii) a nucleic acid fragment encoding all or a portion of a soybean seed storage protein placed in sense or antisense orientation relative to the promoter of (i), and (iii) a transcriptional termination region;

(b) creating a transgenic soybean cell by introducing into a soybean cell the chimeric gene of (a); and (c) growing the transgenic soybean cells of step (b) under conditions that result in expression of the chimeric gene of step (a)

wherein the quantity of one or more members of a class of soybean seed storage protein subunits is reduced when compared to soybeans not containing the chimeric gene of step (a).

DETAILED DESCRIPTION OF THE INVENTION

Brief Description of the Sequence Descriptions

The invention can be more fully understood from the following detailed description and the Sequence Descriptions which form a part of this application. The Sequence Descriptions contain the three letter codes for amino acids as defined in 37 C.F.R. 1.822 which are incorporated herein by reference.

SEQ ID NO:1 shows the 5' to 3' nucleotide sequence encoding the α subunit of the β-conglycinin soybean seed storage protein.

SEQ ID NO:2 shows the 5' to 3' nucleotide sequence encoding the α' subunit of the β-conglycinin soybean seed storage protein.

SEQ ID NO:3 shows the 5' to 3' nucleotide sequence encoding the β subunit of the β-conglycinin soybean seed storage protein.

SEQ ID NOS:4 and 5 show the nucleotide sequences of the PCR primers ConS and Con1.4a (respectively) used to isolate nucleic acid fragments encoding the α and α' subunits of the β-conglycinin soybean seed storage protein.

SEQ ID NOS:6 and 7 show nucleotide sequences of the PCR primers Con.09 and Con.8 (respectively) used to distinguish nucleic acid fragments encoding the α and α' subunits of the β-conglycinin soybean seed storage protein.

SEQ ID NOS:8 and 9 show the nucleotide sequences of the PCR primers ConSa and Con1.9a (respectively) used to isolate full length cDNAs encoding the α and α' subunits of the β-conglycinin soybean seed storage protein.

SEQ ID NO:10 shows the nucleotide sequence of the PCR primer Con.1.0 used to confirm the full length cDNA encoding the α and α' subunits of the β-conglycinin soybean seed storage protein.

SEQ ID NOS:11, 12 and 13 show the 5' to 3' nucleotide sequences encoding the Gy1, Gy2 and Gy3 subunits (respectively) of the group I glycinin soybean seed storage protein.

SEQ ID NOS:14 and 15 show the 5' to 3' nucleotide sequences encoding the Gy4 and Gy5 subunits (respectively) of the group II glycinin soybean seed storage protein.

SEQ ID NOS:16, 17 and 18 show the nucleotide sequences of the PCR primers G1-1, G1-1039 and G1-1475 (respectively) used to isolate the cDNAs encoding the subunits of the group I glycinin soybean seed storage protein.

SEQ ID NOS:19, 20 and 21 show the nucleotide sequences of the PCR primers G4-7, G4-1251, and G4-1670 (respectively) used to isolate the cDNA encoding the subunits of the group II glycinin soybean seed storage protein.

BIOLOGICAL DEPOSITS

Figure 1:
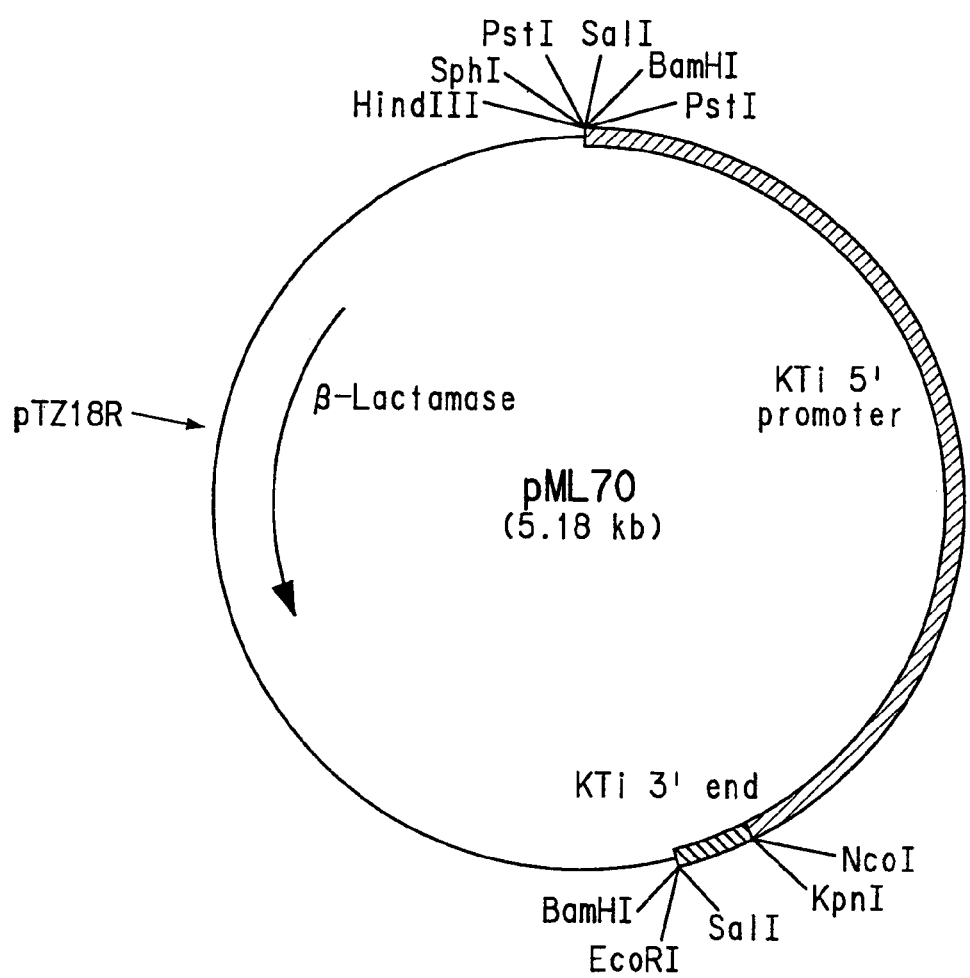
FIG. 1 is a restriction map of plasmid pML70, used as an intermediate cloning vehicle in construction of chimeric genes of the instant invention.

The following plasmids have been deposited under the terms of the Budapest Treaty at American Type Culture Collection (ATCC), 10801 University Boulevard, Manassas, Va. 20110-2209, and bear the following accession numbers:

| Plasmid | Accession Number | Date of Deposit |
| --- | --- | --- |
| pJo1 | ATCC 97614 | Jun. 15, 1996 |
| pBS43 | ATCC 97619 | Jun. 19, 1996 |
| pJo3 | ATCC 97615 | Jun. 15, 1996 |

DEFINITIONS

In the context of this disclosure, a number of terms shall be used. The term "nucleic acid" refers to a large molecule which can be single-stranded or double-stranded, composed of monomers (nucleotides) containing a sugar, a phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to the sequence of DNA or RNA polymers, which can be single- or double-stranded, optionally containing synthetic, non-natural or altered nucleotide bases capable of incorporation into DNA or RNA polymers.

As used herein, the term "homologous to" refers to the relatedness between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.); or by the comparison of sequence similarity between two nucleic acids or proteins, such as by the method of Needleman et al. ((1970) *J. Mol. Biol.* 48:443-453).

As used herein, "essentially similar" refers to DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which results in the production of a chemically equivalent amino acid at a given site, are contemplated; thus, a codon for the amino acid alanine, a hydrophobic amino acid, may be substituted by a codon encoding another hydrophobic amino acid residue such as glycine, valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity of the encoded products. Moreover, the skilled artisan recognizes that "essentially similar" sequences encompassed by this invention can also defined by their ability to hybridize, under stringent conditions (0.1×SSC, 0.1% SDS, 65° C.), with the sequences exemplified herein.

"Gene" refers to a nucleic acid fragment that expresses a specific protein, including regulatory sequences preceding (5' non-coding) and following (3' non-coding) the coding region. "Native" gene refers to an isolated gene with its own regulatory sequences as found in nature. "Chimeric gene" refers to a gene that comprises heterogeneous regulatory and coding sequences not found in nature. "Endogenous" gene refers to the native gene normally found in its natural location in the genome and is not isolated. A "foreign" gene refers to a gene not normally found in the host organism but that is introduced by gene transfer.

"Coding sequence" or "coding region" refers to a DNA sequence that codes for a specific protein and excludes the non-coding sequences. It may constitute an "uninterrupted coding sequence", i.e., lacking an intron or it may include one or more introns bounded by appropriate splice junctions. An "intron" is a nucleotide sequence that is transcribed in the primary transcript but that is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the coding sequence uninterrupted by introns between initiation and termination codons that encodes an amino acid sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, introns, or the coding sequence.

As used herein, "suitable regulatory sequences" refer to nucleotide sequences in native or chimeric genes that are located upstream (5'), within, or downstream (3') to the nucleic acid fragments of the invention, which control the expression of the nucleic acid fragments of the invention. The term "expression", as used herein, refers to the transcription and stable accumulation of the sense (mRNA) or the antisense RNA derived from the nucleic acid fragment(s) of the invention that, in conjunction with the protein apparatus of the cell, results in altered phenotypic traits. Expression of the gene involves transcription of the gene and translation of the mRNA into precursor or mature proteins. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a foreign gene which has substantial homology to an endogenous gene resulting in the suppression of expression of both the foreign and the endogenous gene. "Altered levels" refers to the production of gene product(s) in transgenic organisms in amounts or proportions that differ from that of normal or non-transformed organisms. The skilled artisan will recognize that the phenotypic effects contemplated by this invention can be achieved by alteration of the level of gene product(s) produced in transgenic organisms relative to normal or non-transformed organisms, namely a reduction in gene expression mediated by antisense suppression or cosuppression.

"Promoter" refers to a DNA sequence in a gene, usually upstream (5') to its coding sequence, which controls the expression of the coding sequence by providing the recognition for RNA polymerase and other factors required for proper transcription. In artificial DNA constructs, promoters can also be used to transcribe antisense RNA. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryogenesis, respectively.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

The term "operably linked" refers to nucleic acid sequences on a single nucleic acid molecule which are associated so that the function of one is affected by the other. For example, a promoter is operably linked with a structural gene when it is capable of affecting the expression of that structural gene (i.e., that the structural gene is under the transcriptional control of the promoter).

"Transformation" refers to the transfer of a nucleic acid fragment into the genome of a host organism, resulting in genetically stable inheritance. Host organisms containing the transformed nucleic acid fragments are referred to as "transgenic" organisms.

This invention concerns the construction of transgenic soybean lines wherein the expression of genes encoding seed storage proteins are modulated to effect a change in seed storage protein profile of transgenic plants. Modification of the seed storage protein profile can result in production of novel soy protein products with unique and valuable functional characteristics.

Gene expression in plants uses regulatory sequences that are functional in such plants. The expression of foreign genes in plants is well-established (De Blaere et al. (1987) *Meth. Enzymol.* 153:277-291). The source of the promoter chosen to drive the expression of the fragments of the invention is not critical provided it has sufficient transcriptional activity to accomplish the invention by decreasing the expression of the target seed storage protein genes. Preferred promoters include strong constitutive plant promoters, such as those directing the 19S and 35S transcripts in cauliflower mosaic virus (Odell, J. T. et al. (1985) *Nature* 313:810-812; Hull et al. (1987) *Virology* 86:482-493). Particularly preferred promoters are those that allow seed-specific expression. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al. (1984) *Ann. Rev. Plant Physiol.* 35:191-221; Goldberg et al. (1989) *Cell* 56:149-160). Moreover, different seed storage proteins may be expressed at different stages of seed development.

Expression of seed-specific genes has been studied in great detail (See reviews by Goldberg et al. (1989) *Cell* 56:149-160 and Higgins et al. (1984) *Ann. Rev. Plant Physiol.* 35:191-221). There are currently numerous examples of seed-specific expression of seed storage protein genes (natural or chimeric) in transgenic dicotyledonous plants; in general, temporal and spatial expression patterns are maintained. The promoters used in such examples could potentially be used to affect the present invention. These include genes from dicotyledonous plants for bean β-phaseolin (Sengupta-Gopalan et al.(1985) *Proc. Natl. Acad. Sci. USA* 82:3320-3324; Hoffman et al. (1988) *Plant Mol. Biol.* 11:717-729), bean lectin (Voelker et al. (1987) *EMBO J.* 6:3571-3577), soybean lectin (Okamuro et al. (1986) *Proc. Natl. Acad. Sci. USA* 83:8240-8244), soybean Kunitz trypsin inhibitor (Perez-Grau et al. (1989) *Plant Cell* 1:095-1109), soybean β-conglycinin (Beachy et al. (1985) *EMBO J.* 4:3047-3053; pea vicilin (Higgins et al. (1988) *Plant Mol. Biol.* 11:683-695), pea convicilin (Newbigin et al. (1990) *Planta* 180:461-470), pea legumin (Shirsat et al. (1989) *Mol. Gen. Genetics* 215:326-331), rapeseed napin (Radke et al. (1988) *Theor. Appl. Genet.* 75:685-694) and *Arabidopsis thaliana* 2S albumin (Vandekerckhove et al. (1989) *Bio/Technology* 7:929-932).

Of particular use in the expression of the nucleic acid fragment of the invention will be the heterologous promoters from several soybean seed storage protein genes such as those for the Kunitz trypsin inhibitor (KTi; Jofuku et al. (1989) *Plant Cell* 1:1079-1093; glycinin (Nielson et al. (1989) *Plant Cell* 1:313-328), and β-conglycinin (Harada et al. (1989) *Plant Cell* 1:415-425). The skilled artisan will recognize that attention must be paid to differences in temporal regulation endowed by different seed promoters. For example, the promoter for the α-subunit gene is expressed a few days before that for the β-subunit gene (Beachy et al. (1985) *EMBO J.* 4:3047-3053), so that the use of the β-subunit gene is likely to be less useful for suppressing α-subunit expression.

Also of potential use, but less preferred, will be the promoters of genes involved in other aspects of seed metabolism, such as lipid or carbohydrate biosynthesis. In summary, the skilled artisan will have no difficulty in recognizing that any promoter of sufficient strength and appropriate temporal expression pattern can potentially be used to implement the present invention. Similarly, the introduction of enhancers or enhancer-like elements into the promoter regions of either the native or chimeric nucleic acid fragments of the invention would result in increased expression to accomplish the invention. This would include viral enhancers such as that found in the 35S promoter (Odell et al. (1988) *Plant Mol. Biol.* 10:263-272), enhancers from the opine genes (Fromm et al. (1989) *Plant Cell* 1:977-984), or enhancers from any other source that result in increased transcription when placed into a promoter operably linked to the nucleic acid fragment of the invention.

Of particular importance is the DNA sequence element isolated from the gene encoding the α-subunit of β-conglycinin that can confer a 40-fold, seed-specific enhancement to a constitutive promoter (Chen et al. (1989) *Dev. Genet.* 10:112-122). One skilled in the art can readily isolate this element and insert it within the promoter region of any gene in order to obtain seed-specific enhanced expression with the promoter in transgenic plants. Insertion of such an element in any seed-specific gene that is normally expressed at times different than the β-conglycinin gene will result in expression of that gene in transgenic plants for a longer period during seed development.

Any 3' non-coding region capable of providing a polyadenylation signal and other regulatory sequences that may be required for the proper expression of the nucleic acid fragments of the invention can be used to accomplish the invention. This would include 3' ends of the native fatty acid desaturase(s), viral genes such as from the 35S or the 19S cauliflower mosaic virus transcripts, from the opine synthesis genes, ribulose 1,5-bisphosphate carboxylase, or chlorophyll a/b binding protein. There are numerous examples in the art that teach the usefulness of different 3' non-coding regions.

Various methods of transforming cells of higher plants according to the present invention are available to those skilled in the art (see European Patent Publications EP-A-295,959 and EP-A-318,341). Such methods include those based on transformation vectors utilizing the Ti and Ri plasmids of *Agrobacterium* spp. It is particularly preferred to use the binary type of these vectors. Ti-derived vectors transform a wide variety of higher plants, including monocotyledonous and dicotyledonous plants (Sukhapinda et al. (1987) *Plant Mol. Biol.* 8:209-216; Potrykus, (1985) *Mol. Gen. Genet.* 199:183). Other transformation methods are available to those skilled in the art, such as direct uptake of foreign DNA constructs (see European Patent Publication EP-A-295,959), techniques of electroporation (Fromm et al. (1986) *Nature (London)* 319:791) or high-velocity ballistic bombardment with metal particles coated with the nucleic acid constructs (Klein et al. (1987) *Nature (London)* 327: 70). Once transformed, the cells can be regenerated by those skilled in the art. Of particular relevance are the recently described methods to transform soybean, including McCabe et al. ((1988) *Bio/Technology* 6:923-926), Finer et al. ((1991) *In Vitro Cell. Dev. Biol.* 27:175-182) and Hinchee, M. A. W. ((1988) *Bio/Technology* 6:915-922).

Once transgenic plants are obtained by one of the methods described above, it is necessary to screen individual transgenics for those that most effectively display the desired phenotype. It is well known to those skilled in the art that individual transgenic plants carrying the same construct may differ in expression levels; this phenomenon is commonly referred to as "position effect". Thus, in the present invention different individual transformants may vary in the effectiveness of suppression of the target seed protein. The person skilled in the art will know that special considerations are associated with the use of antisense or cosuppression technologies in order to reduce expression of particular genes. U.S. Pat. Nos. 5,190,931, 5,107,065 and 5,283,323 have taught the feasibility of these techniques, but it is well known that their efficiency is unpredictable. Accordingly, the person skilled in the art will make multiple genetic constructs containing one or more different parts of the gene to be suppressed, since the art does not teach a method to predict which will be most effective for a particular gene.

Furthermore, even the most effective constructs will give an effective suppression phenotype only in a fraction of the individual transgenic lines isolated. For example, World Patent Publications WO93/11245 and WO94/11516 teach that when attempting to suppress the expression of fatty acid desaturase genes in canola, actual suppression was obtained in less than 1% of the lines tested. In other species the percentage is somewhat higher, but in no case does the percentage reach 100. This should not be seen as a limitation on the present invention, but instead as practical matter that is appreciated and anticipated by the person skilled in this art. Accordingly, the skilled artisan will develop methods for screening large numbers of transformants. The nature of these screens will generally be chosen on practical grounds, and is not an inherent part of the invention. A preferred method will be one which allows large numbers of samples to be processed rapidly, since it will be expected that the majority of samples will be negative.

The mechanism of cosuppression remains unclear (for one review and speculation, see Flavell, R. (1994) *Proc. Natl. Acad. Sci. USA* 91:3490-3496), and therefore the exact requirments to induce it when desired are also unclear. Most examples found in the literature involve the use of all or a large part of the transcribed region of the gene to be cosuppressed to elicit the desired response. However, in at least one case (Brusslan et al. (1993) *Plant Cell* 5:667-677; Brusslan and Tobin (1995) *Plant Mol. Biol.* 27:809-813), that of the cab140 gene of Arabidopsis, the use of the promoter (as a 1.3 kb fragment) and just 14 bp of transcribed region fused to a completely unrelated gene was sufficient to result in cosuppression of the endogenous cab140 gene as well as the introduced chimeric gene. This result is unusual and apparantly quite unpredictable, as numerous other promoter-leader (the 5' untranslated leader being defined as the region between the start of transcription and the translation initiation codon) units have been used to drive chimeric genes successfully. Flavell speculates that some or many genes (including members of multigene families such as those encoding seed proteins) may have evolved so as to avoid the mechanisms of cosuppression, while others have not, providing a potential further level of regulation as genomes evolve. Thus, the instant observation that the promoter and leader of the conglycinin gene can be used to suppress expression of endogenous conglycins while the other portion of the transgene (beyond the initiation codon) can be used to suppress a completely unrelated gene is unique.

EXAMPLES

The present invention is further defined by the following examples. It will be understood that the examples are given for illustration only and the present invention is not limited to uses described in the examples. The present invention can be used to generate transgenic soybean plants with altered levels of various seed storage proteins. From the above discussion and the following examples, one skilled in the art can ascertain, and without departing from the spirit and scope thereof, can make various changes and modifications of the invention to adapt it to various usages and conditions. All such modifications are intended to fall within the scope of the intended claims.

Detailed procedures for DNA manipulation, such as use of restriction endonuclease enzymes, other modifying enzymes, agarose gel electrophoresis, nucleic acid hybridization, and transformation of *E. coli* with plasmid DNA are described in Sambrook et al. (1989) Molecular Cloning, A Laboratory manual, 2nd ed, Cold Spring Harbor Laboratory Press (hereinafter "Maniatis"). All restriction enzymes and other modifying enzymes were obtained from Gibco BRL (Gaithersburg, Md.).

Example 1

To determine whether the expression of β-conglycinin in developing soybean cotyledons could be the target of cosuppression, truncated cDNA fragments of the α and α' subunits of β-conglycinin were prepared using a reverse transcriptase polymerase chain reaction kit (Geneamp™ RNA PCR Kit; Perkin Elmer Cetus). The upper primer, ConS, is homologous to nucleotides 5-19 of the α and α' subunit cDNA sequences obtained from the EMBL/GenBank/DDBJ databases. To aid cloning, additional nucleotides were added to the 5' end to code for an Nco I restriction site. The lower primer, Con 1.4a, is complementary to nucleotides 1370-1354 of SEQ ID NO:1 and 1472-1456 of SEQ ID NO:2, representing the sequences of the α and α' cDNAs, respectively. To aid in cloning, additional nucleotides were added to the 5' end to introduce a Kpn I restriction site. The nucleotide sequences of PCR primers ConS and Con1.4a are shown below.

```
ConS
5'-CGTACCATGGTGAGAGCGCGGTTCC-3'        (SEQ ID NO:4)
      Nco I

Con1.4a
5'-CGGTACCGAATTGAAGTGTGGTAG-3'         (SEQ ID NO:5)
    Kpn I
```

RNA isolated from developing soybean seeds was reverse-transcribed using either the kit-supplied random hexamers, or Con1.4a, following the manufacturer's protocol. The resulting cDNA fragments were amplified in the PCR (Polymerase Chain Reaction) reaction using a mixture of ConS and Con1.4a. Reactant concentrations were as described in the manufacturer's protocols. The following program was used: a) one cycle of 2 minutes at 95° C.; b) 35 cycles of: 1.5 minutes at 50° C. (annealing), 5 minutes at 70° C. (extension), 1.5 minutes at 95° C. (denaturation); and c) one cycle of 2 minutes at 50° C. followed by 10 minutes at 68° C. Fifteen microliters of each of the PCR reaction mixes was analyzed by agarose gel electrophoresis. Reactions resulted in PCR products of the expected sizes: 1.47 kb for α' and 1.37 kb for α. The truncated cDNA fragments from the remainder of the reaction mixes were purified using the Wizard™ PCR Preps DNA Purification System kit (Promega).

Figure 2:
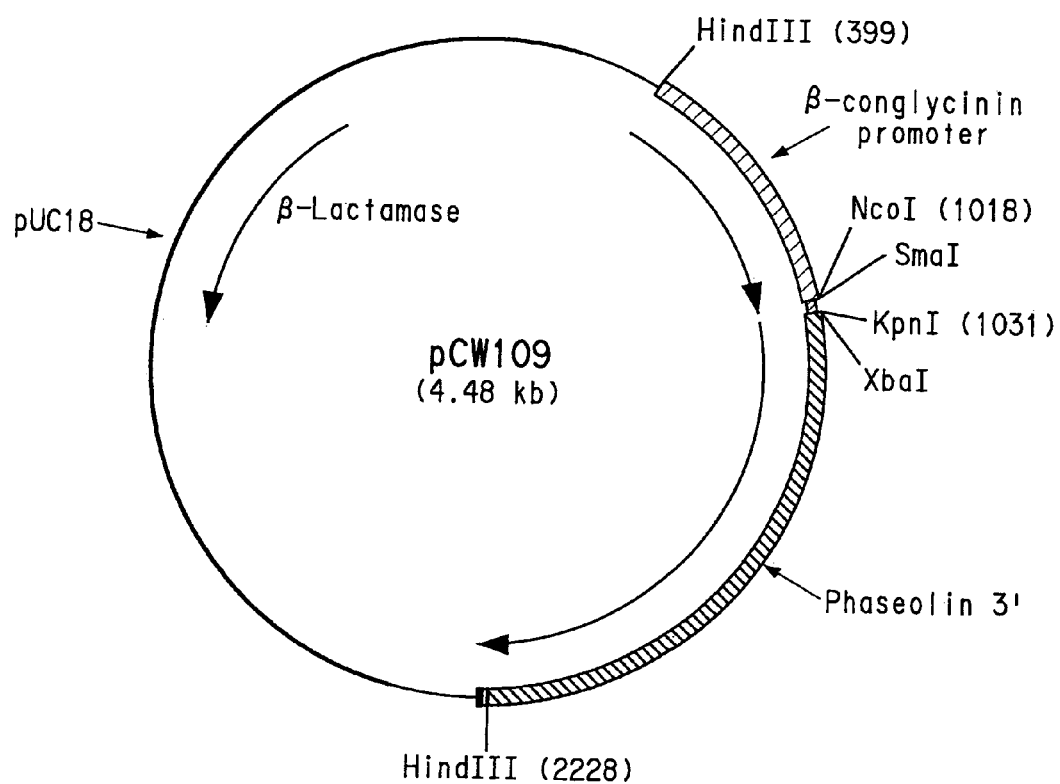
FIG. 2 is a restriction map of plasmid pCW109, used as an intermediate cloning vehicle in construction of chimeric genes of the instant invention.

The purified reaction mix containing the α and α' fragments, which because of the primers used, included Nco I restriction sites at the 5' ends and Kpn I restriction sites at the 3' ends, were digested with Kpn I and Nco I restriction enzymes. The α cDNA fragment was recovered following gel electrophoresis, designated as fragment F8, and directionally cloned (sense orientation) into pCW109 (FIG. 1) and pML70 (FIG. 2) using the Nco I to Kpn I sites present in both plasmids. F8 was confirmed as α by PCR using a nested set of primers (Con.09 and Con.8) internal to ConS and Con1.4a, and distinguished from α' by digestion of pCW109/F8 plasmid with Hind III, Nco I, Kpn I, and Pst I (α does not contain a Pst I site whereas α' does).

```
Con.09
5'-TCGTCCATGGAGCGCGGTTCCCATTAC-3'      (SEQ ID NO:6)

Con.8
5'-TCTCGGTCGTCGTTGTT-3'                (SEQ ID NO:7)
```

Figure 3:
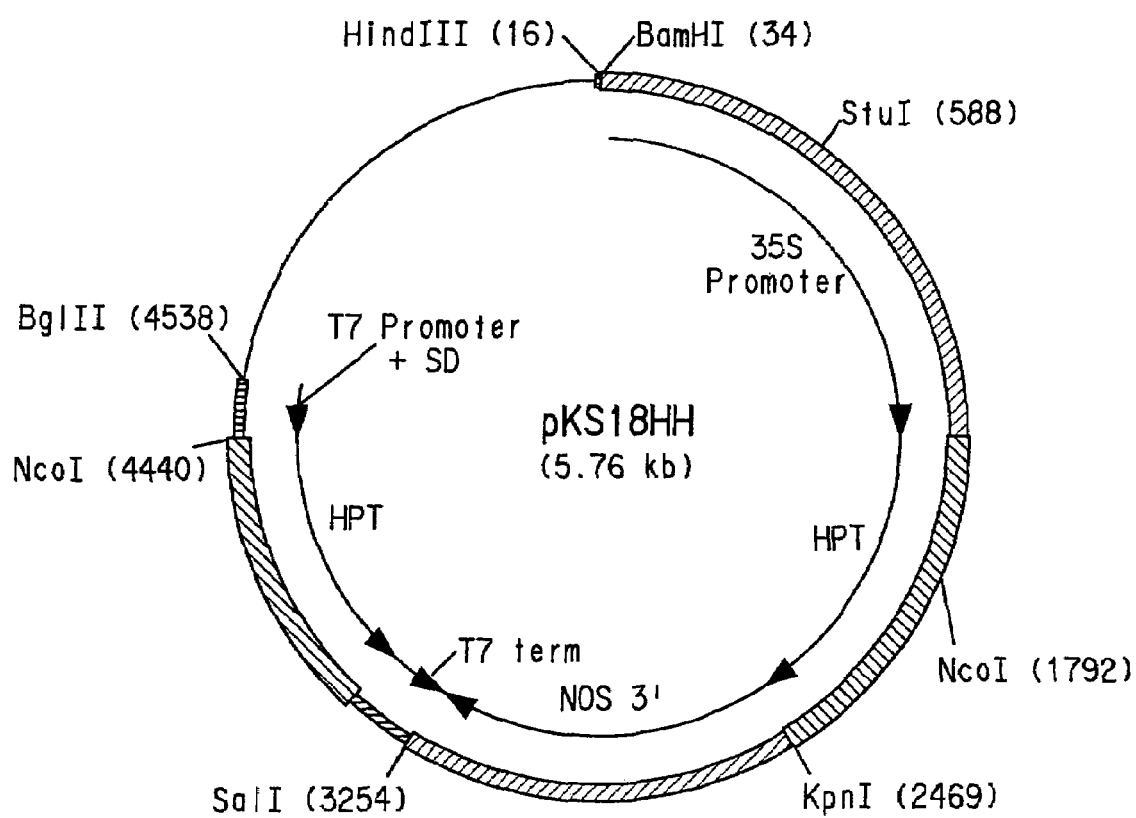
FIG. 3 is a restriction map of plasmid pKS18HH, used as an intermediate cloning vehicle in construction of chimeric genes of the instant invention.

The transcriptional unit KTi promoter/truncated α/KTi 3' end was released from plasmid pML70/F8 by restriction digest with BamHI, gel isolated, and labeled as F11. F11 was then cloned into pKS18HH (FIG. 3) at the BamH I site. pKS18HH is a plasmid construction containing the following genetic elements: (i) T7 promoter/Hygromycin B Phosphotransferase (HPT)/T7 Terminator Sequence; (ii) 35S promoter from cauliflower mosaic virus (CaMV)/Hygromycin B Phosphotransferase (HPT)/Nopaline Synthase (NOS) 3' from *Agrobacterium* tumefaciens T-DNA; and (iii) pSP72 plasmid vector (Promega) with beta-lactamase coding region removed. One skilled in the art of molecular biology can ligate the above three components into a single plasmid vector using well known protocols (Maniatis).

Figure 4:
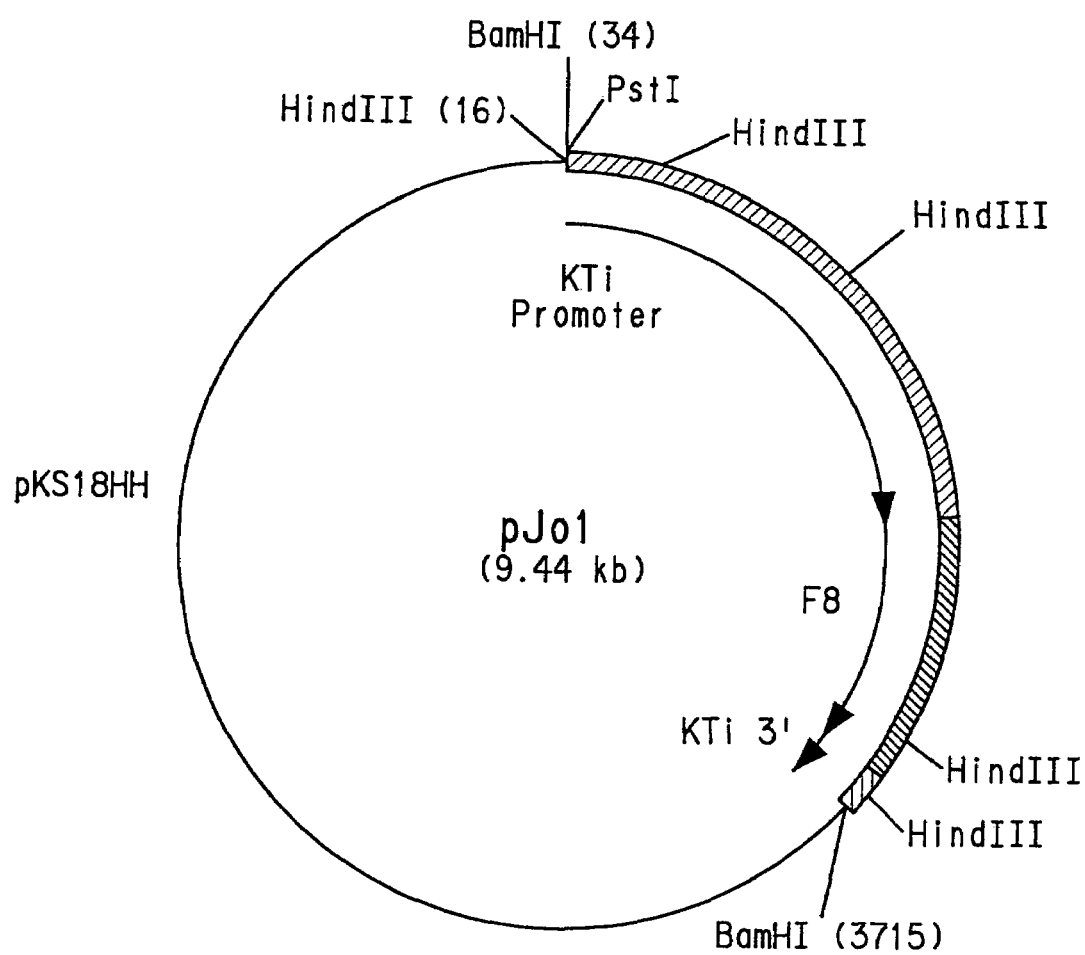
FIG. 4 is a restriction map of plasmid pJo1. This plasmid was derived by cloning the plant transcriptional unit KTi promoter/truncated α subunit of β-conglycinin/KTi 3' end into the BamH I site of pKS18HH.

The Hygromycin B Phosphotransferase (HPT) gene was isolated by PCR amplification from *E. coli* strain W677 containing a Klebsiella-derived plasmid pJR225 (Gritz L., and Davies J. (1983) *Gene* 25:179-188). pKS18HH contains the CaMV 35S/HPT/NOS cassette for constitutive expression of the HPT enzyme in plants, such as soybean. The pKS18HH plasmid also contains the T7 promoter/HPT/T7 terminator cassette for expression of the HPT enzyme in certain strains of *E. coli*, such as NovaBlue™ (DE3) (Novagen) that are lysogenic for lambda DE3 (which carries the T7 RNA Polymerase gene under lacUV5 control). pKS18HH also contains three unique restriction endonuclease sites suitable for cloning of genes into this vector. Thus, the pKS18HH plasmid vector allows the use of Hygromycin B for selection in both *E. coli* and plants. Confirmation of insertion and orientation of the F11 fragment was accomplished by digestion with HindIII. A clone with the F11 fragment in clockwise orientation was selected and labeled pJo1 (FIG. 4).

Transformation of Somatic Embryo Cultures

The following stock solutions and media were used for transformation and propogation of soybean somatic embryos:

| Stock Solutions | | (g/L) | Media |
|---|---|---|---|
| MS Sulfate 100x stock | | | SB55 (per Liter) |
| $MgSO_4$ | $7H_2O$ | 37.0 | 10 mL of each MS stock |
| $MnSO_4$ | $H_2O$ | 1.69 | 1 mL of B5 Vitamin stock |
| $ZnSO_4$ | $7H_2O$ | 0.86 | 0.8 g $NH_4NO_3$ |
| $CuSO_4$ | $5H_2O$ | 0.0025 | 3.033 g $KNO_3$ |
| | | | 1 mL 2,4-D (10 mg/mL stock) |
| MS Halides 100x stock | | | |
| $CaCl_2$ | $2H_2O$ | 44.0 | 0.667 g asparagine |
| KI | | 0.083 | pH 5.7 |
| $CoCl_2$ | $6H_2O$ | 0.00125 | |
| $KH_2PO_4$ | | 17.0 | SB103 (per Liter) |
| $H_3BO_3$ | | 0.62 | 1 pk. Murashige & Skoog salt mixture (Gibco BRL) |
| $Na_2MoO_4$ | $2H_2O$ | 0.025 | 60 g maltose |
| $Na_2EDTA$ | | 3.724 | 2 g gelrite |

-continued

| Stock Solutions | | (g/L) | Media |
|---|---|---|---|
| $FeSO_4$ | $7H_2O$ | 2.784 | pH 5.7 (For SB103 plus charcoal, add 5 g charcoal) |
| B5 Vitamin stock | | | SB148 (per Liter) |
| myo-inositol | | 100.0 | 1 pk. Murashige & Skoog salt mixture (Gibco BRL) |
| nicotinic acid | | 1.0 | 60 g maltose |
| pyridoxine HCl | | 1.0 | 1 mL B5 vitamin stock |
| thiamine | | 10.0 | 7 g agarose |
| | | | pH 5.7 |

Soybean embryonic suspension cultures were maintained in 35 mL liquid media (SB55) on a rotary shaker (150 rpm) at 28° C. with a mix of fluorescent and incandescent lights providing a 16/8 h day/night schedule. Cultures were sub-cultured every 2 to 3 weeks by inoculating approximately 35 mg of tissue into 35 mL of liquid media.

Soybean embryonic suspension cultures were transformed with pJo1 by the method of particle gun bombardment (see Klein et al. (1987) *Nature* 327:70). A DuPont Biolistic™ PDS1000/He instrument was used for these transformations.

Five μL of pJo1 plasmid DNA (1 μg/μL), 50 μL $CaCl_2$ (2.5 M), and 20 μL spermidine (0.1 M) were added to 50 μL of a 60 mg/mL 1 mm gold particle suspension. The particle preparation was agitated for 3 minutes, spun in a microfuge for 10 seconds and the supernatant removed. The DNA-coated particles were then washed once with 400 μL 70% ethanol and resuspended in 40 μL of anhydrous ethanol. The DNA/particle suspension was sonicated three times for 1 second each. Five μL of the DNA-coated gold particles were then loaded on each macro carrier disk.

Approximately 300 to 400 mg of two week old suspension culture was placed in an empty 60 mm×15 mm petri dish and the residual liquid removed from the tissue by pipette. The tissue was placed about 3.5 inches away from the retaining screen and bombarded twice. Membrane rupture pressure was set at 1000 psi and the chamber was evacuated to −28 inches of Hg. Two plates were bombarded per construct per experiment. Following bombardment, the tissue was divided in half and placed back into liquid media and cultured as described above.

Fifteen days after bombardment, the liquid media was exchanged with fresh SB55 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, plus 0.5% charcoal to begin maturation. After 1 week, embryos were transferred to SB103 media minus charcoal. After 3 weeks on SB103 media, maturing embryos were separated and placed onto SB148 media. Conditions during embryo maturation were 26° C., with a mix of fluorescent and incandescent lights providing a 16/8 h day/night schedule. After 6 weeks on SB148 media, embryos were analyzed for the expression of the β-conglycinin subunit proteins. Each embryonic cluster gave rise to 5 to 20 somatic embryos.

Analysis of Transformed Somatic Embryos

Initial experiments were performed to determine when the α, α' and β subunits of β-conglycinin could be visualized during somatic embryo maturation by SDS-PAGE gel electrophoresis. Cotyledons of non-transformed embryos (generated as above, except they did not undergo bombardment) were dissected from embryos at 6, 8, 10, and 12 weeks after initiating maturation and kept frozen at −80° C. until analyzed. Cotyledonary tissue was weighed, 10 μL/mg tissue of extraction buffer was added, and the tissue ground in a Pellet Pestle Disposable Mixer (Kimble/Kontes). Extraction buffer consisted of 50 mM Tris-HCl (pH 7.5), 10 mM β-mercaptoethanol (BME), and 0.1% SDS. The samples were then microfuged at 12,000 rpm for 10 minutes and supernatant remove to a new microfuge tube by pipette. Extracts were kept frozen at −20° C. until used.

For SDS-PAGE analysis, 8 μL of (2×) loading buffer was added to 8 μL of sample extract. The (2×) loading buffer consisted of 100 mM Tris-HCl (pH 7.5), 4% SDS, 0.2% bromophenol blue, 15% glycerol, and 200 mM βME. The mixture was heated at 95° C. for 4 minutes. Sample mixes were then microfuged (12,000 rpm for 20 seconds) and loaded onto a 10% precast Ready Gel™ (Bio-Rad) that was assembled into a mini-Protein II Electrophoresis Cell (Bio-Rad). Bio-Rad Tris/Glycine/SDS Buffer was used as the running buffer and voltage was a constant 125V. In addition to sample extracts, each gel contained one lane with a molecular weight standard (Bio-rad SDS-PAGE standard, low range) and one lane with total soybean seed protein extracted from commercial defatted soy flour. Upon completion, the gels were stained with Coomassie Brilliant Blue and destained (Maniatis) in order to visualize proteins. Gels were photographed, placed in a sealed bag with water, and stored in the refrigerator. Results indicated that the α, α' and β subunits of β-conglycinin were detectable in the cotyledons of somatic embryos between 8 and 10 weeks after the start of maturation.

Analysis of transformed embryos was carried out at 10 weeks after the start of maturation using the methods described above. Two embryos per clone were analyzed initially. Additional embryos were analyzed if suppression of the β-conglycinin subunits observed in the two embryos. Table 1 presents the results of this analysis, wherein the presence or absence of each β-conglycinin subunit is indicated by a (+) or (−), respectively.

TABLE 1

| Clone | Embryo | α | α' | β |
|---|---|---|---|---|
| Jo1-1 | 1 | − | − | + |
| | 2 | − | − | + |
| | 3 | + | + | + |
| | 4 | − | − | + |
| | 5 | + | + | + |
| Jo1-2 | 1 | + | + | + |
| | 2 | + | + | + |
| Jo1-3 | 1 | + | + | + |
| | 2 | + | + | + |
| Jo1-4 | 1 | − | − | − |
| | 2 | − | − | − |
| | 3 | − | − | − |
| | 4 | + | + | + |
| | 5 | − | − | − |
| Jo1-5b | 1 | + | + | + |
| | 2 | + | + | + |
| Jo1-5c | 1 | − | − | + |
| | 2 | + | + | + |
| Jo1-5d | 1 | + | + | + |
| | 2 | + | + | + |
| Jo1-6a | 1 | − | − | + |
| | 2 | − | − | + |
| | 3 | − | − | + |
| | 4 | − | − | + |
| | 5 | + | + | + |
| Jo1-6b | 1 | + | + | + |
| | 2 | + | + | + |
| Jo1-6c | 1 | + | + | + |
| Jo1-6d | 1 | + | + | + |
| | 2 | + | + | + |
| Jo1-6d | 1 | + | + | + |
| | 2 | + | + | + |
| Jo1-6e | 1 | + | + | + |
| | 2 | + | + | + |
| Jo1-7a | 1 | − | − | + |
| | 2 | + | + | + |
| Jo1-7b | 1 | − | − | + |
| Jo1-8a | 1 | + | + | + |
| Jo1-8b | 1 | + | + | + |
| | 2 | + | + | + |
| Jo1-9a | 1 | + | + | + |
| | 2 | + | + | + |
| Jo1-9b | 1 | + | + | + |
| | 2 | − | − | + |
| Jo1-9c | 1 | + | + | + |
| Jo1-10 | 1 | − | − | + |
| | 2 | + | + | + |

Seven transgenic clones gave rise to embryos in which the expression α and α' was suppressed. In addition, one clone (Jo1-4) gave rise to embryos in which all three β-conglycinin subunits were suppressed. This result is surprising as the truncated α transgene sequence overlaps with only a 0.75 kb portion of the total 1.32 kb β subunit cDNA. Overall, there is only 52% similarity between the truncated α transgene and the β subunit cDNA. With the knowledge at hand, the truncated α transgene would not be considered to possess sufficient similarity of stucture to "cosuppress" the β subunit of the β-conglycinin gene.

Figure 5:
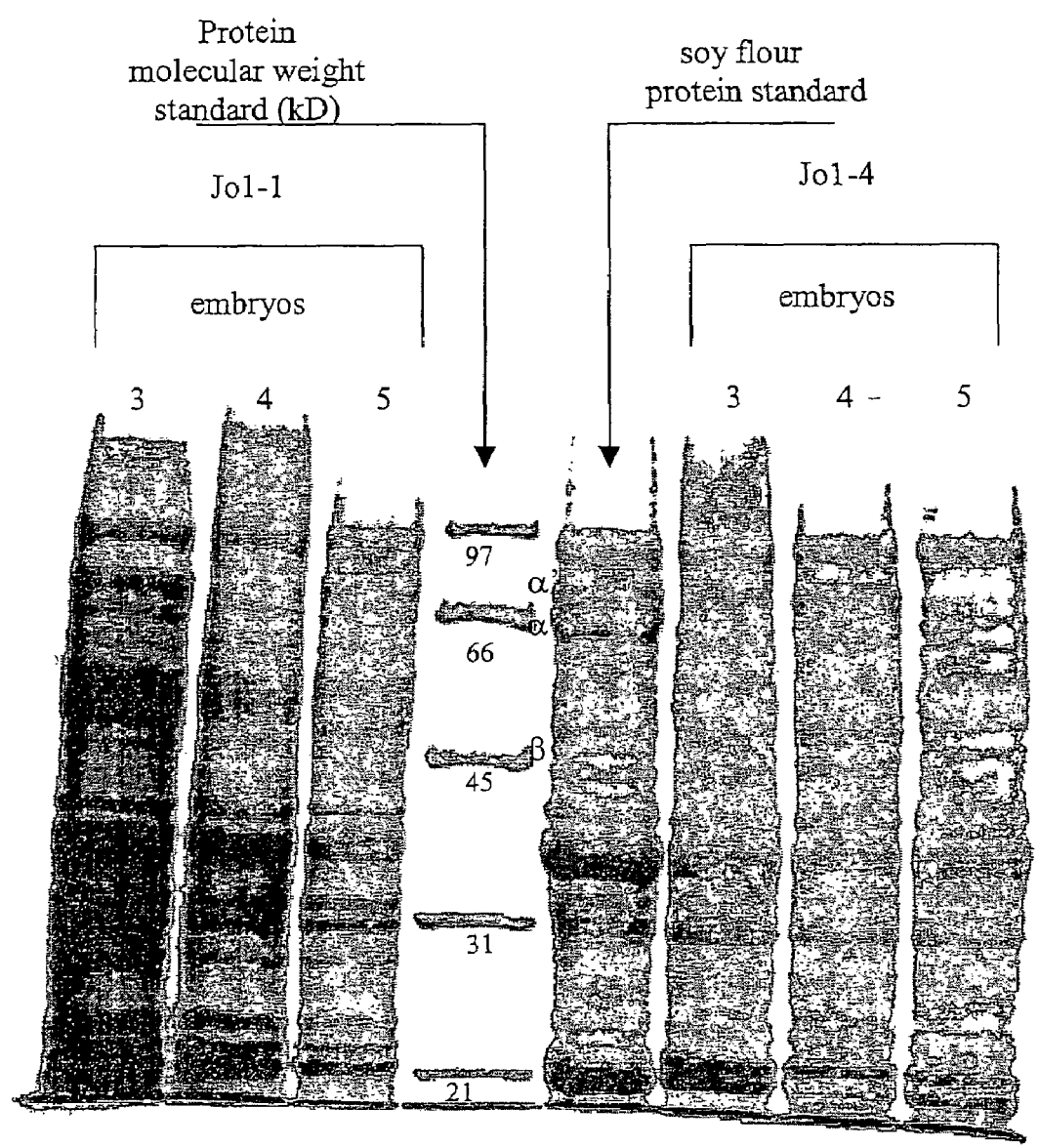
FIG. 5 is an SDS-PAGE gel of extracted protein from somatic embryos transformed with pJo1.

An example of an SDS-PAGE analysis is shown in FIG. 5. Lanes 1-3 are extracts of three cotyledons dissected from embryos generated from clone Jo1-1. Lanes 4 and 5 are protein molecular weight standards and soy protein standard derived from seed, respectively. Lanes 6-8 are extracts of cotyledons dissected from embryos generated from clone Jo1-4. The protein pattern in lane 2 is an example of embryos in which both α and α' are co-suppressed. The protein patterns in lanes 6 and 8 are examples of embryos where all the subunits comprising β-conglycinin are suppressed.

Example 2

To determine if expression of β-conglycinin could be suppressed in developing cotyledons by cosuppression using the β-conglycinin promoter region, a plasmid, designated pBS43, containing a *Glycine max* microsomal delta-12 desaturase cDNA (GmFad 2-1) sequence (Heppard et al., (1996) *Plant Physiol.* 110:311-319; GenBank Acc. No. L43920) under control of the soybean β-conglycinin promoter (Beachy et al., (1985) *EMBO J.* 4:3047-3053), was constructed. The construction of this vector was facilitated by the use of the following plasmids: pMH40, pCST2 and pBS13. The plasmid constructions detailed below are described in part in U.S. patent application Ser. No. 08/262, 401 and World Patent Publication No. WO94/11516, both of which are incorporated herein by reference.

The pMH40 vector was derived from plasmid pGEM9z, a commercially available cloning vector (Promega Biotech) by the insertion a 1.4 kb 35S promoter region from CaMV (Odell et al. (1985) *Nature* 303:810-812; Harpster et al. (1988) *Mol. Gen. Genet.* 212:182-190) coupled to the β-glucuronidase gene from *E. coli*. This was a 1.85 kb fragment encoding the enzyme β-glucuronidase (Jefferson et al. (1986) *PNAS USA* 83:8447-8451) and a 0.3 kb DNA fragment containing the transcription terminator from the nopaline synthase gene of the Ti-plasmid of *Agrobacterium tumefaciens* (Fraley et al. (1983) *PNAS USA* 80:4803-4807).

The vector pCST2 was derived from vectors pML18 and pCW109A. The plasmid pCW109A contains the soybean β-conglycinin promoter sequence and the phaseolin 3' untranslated region and is a modified version of vector pCW109 which was derived from the commercially available plasmid pUC18 (Gibco-BRL). The vector pCW109 was made by inserting into the Hind III site of the cloning vector pUC18a 555 bp 5' non-coding region (containing the promoter region) of the β-conglycinin gene followed by the multiple cloning sequence containing the restriction endonuclease sites for Nco I, Sma I, Kpn I and Xba I, then 1174 bp of the common bean phaseolin 3' untranslated region into the Hind III site. The β-conglycinin promoter region used is an allele of the published β-conglycinin gene (Doyle et al., (1986) *J. Biol. Chem.* 261:9228-9238) due to differences at 27 nucleotide positions. Further sequence description of this gene may be found World Patent Publication WO91/13993.

To facilitate use in antisense constructions, the Nco I site and potential translation start site in the plasmid pCW109 was destroyed by digestion with Nco I, mung bean exonuclease digestion and religation of the blunt site to give the modified plasmid pCW109A.

The vector pML18 consists of the non-tissue specific and constitutive cauliflower mosaic virus (35S) promoter (Odell et al., (1985) *Nature* 313:810-812; Hull et al., (1987) *Virology* 86:482-493), driving expression of the neomycin phosphotransferase gene (Beck et al. (1982) *Gene* 19:327-336) followed by the 3' end of the nopaline synthase gene including nucleotides 848 to 1550 (Depicker et al. (1982) *J. Appl. Genet.* 1:561-574). This transcriptional unit was inserted into the commercial cloning vector pGEM9z (Gibco-BRL) and is flanked at the 5' end of the 35S promoter by the restriction sites Sal I, Xba I, Bam HI and Sma I, in that order. An additional Sal I site is present at the 3' end of the NOS 3' sequence and the Xba I, Bam HI and Sal I sites are unique. The plasmid pML18 was digested with Xba I, the singled stranded ends were filled-in using the Klenow fragment of DNA polymerase I, and the product was ligated in order to remove the Xba I site. The resulting plasmid was designated pBS16.

The plasmid pCW109A was digested with Hind III and the resulting 1.84 kb fragment, which contained the β-conglycinin/antisense delta-12 desaturase cDNA/phaseolin 3' untranslated region, was gel isolated. This 1.84 kb fragment was ligated into the Hind III site of pBS16. A plasmid containing the insert in the desired orientation yielded a 3.53 kb and 4.41 kb fragment when digested with Kpn I and this plasmid was designated pCST2.

The vector pBS13 was used as the source of the GmFad2-1 cDNA, which encodes the soybean microsomal delta12-desaturase and possesses the sequence as disclosed in GenBank Acc. No. L43920. The vector pBS13 was derived from the vector pML70 (FIG. 1), which contains the KTi3 promoter and the KTi3 3' untranslated region and was derived from the commercially available vector pTZ18R (Pharmacia) via the intermediate plasmids pML51, pML55, pML64 and pML65. A 2.4 kb Bst BI/Eco RI fragment of the complete soybean KTi3 gene (Jofuku and Goldberg (1989) *Plant Cell* 1:1079-1093), which contains all 2039 nucleotides of the 5' untranslated region and 390 bases of the coding sequence of the KTi3 gene ending at the Eco RI site corresponding to bases 755 to 761 of the sequence described in Jofuku (supra), was ligated into the Acc I/Eco RI sites of pTZ18R to create the plasmid pML51. To destroy an Nco I site in the middle of the 5' untranslated region of the KTi3 insert, plasmid pML51 was cut with Nco I, the singled stranded ends were filled-in using the Klenow fragment of DNA polymerase I, and the product was religated resulting in the plasmid pML55. The plasmid pML55 was partially digested with Xmn I/Eco RI to release a 0.42 kb fragment, corresponding to bases 732 to 755 of the above cited sequence, which was discarded. A synthetic Xmn I/Eco RI linker containing an Nco I site, was constructed by making a dimer of complementary synthetic oligonucleotides consisting of the coding sequence for an Xmn I site (5'-TCTTCC-3') and an Nco I site (5'-CCATGGG-3') followed directly by part of an Eco RI site (5'-GAAGG-3'). The Xmn I and Nco I/Eco RI sites were linked by a short intervening sequence (5'-ATAGCCCCCCAA-3'). This synthetic linker was ligated into the Xmn I/Eco RI sites of the 4.94 kb fragment to create the plasmid pML64. The 3' untranslated region of the KTi3 gene was amplified from the sequence described in Jofuku (supra) by standard PCR protocols (Perkin Elmer Cetus, GeneAmp PCR kit) using the primers ML51 and ML52. Primer ML51 contained the 20 nucleotides corresponding to bases 1072 to 1091 of the above cited sequence with the addition of nucleotides corresponding to Eco RV (5-'GATATC-3'), Nco I (5'-CCATGG-3'), Xba I (5'-TCTAGA-3'), Sma I (5'-CCCGGG-3') and Kpn I (5'-GGTACC-3') sites at the 5' end of the primer. Primer ML52 contained to the exact compliment of the nucleotides corresponding to bases 1242 to 1259 of the above cited sequence with the addition of nucleotides corresponding to Sma I (5'-CCCGGG-3'), Eco RI (5'-GAATTC-3'), Bam HI (5'-GGATCC-3') and Sal I (5'-GTCGAC-3') sites at the 5' end of the primer. The PCR-amplified 3' end of the KTi3 gene was ligated into the Nco I/Eco RI sites of pML64 to create the plasmid pML65. A synthetic multiple cloning site linker was constructed by making a dimer of complementary synthetic oligonucleotides consisting of the coding sequence for Pst I (5'-CTGCA-3'), Sal I (5'-GTCGAC-3'), Bam HI (5'-GGATCC-3') and Pst I (5'-CTGCA-3') sites. The linker was ligated into the Pst I site (directly 5' to the KTi3 promoter region) of pML65 to create the plasmid pML70.

The 1.46 kb Sma I/Kpn I fragment from soybean delta-12 desaturase cDNA, GmFad2-1 (GenBank Acc. No. L43920), was ligated into the corresponding sites in pML70 resulting in the plasmid pBS10. The desaturase cDNA fragment was in the reverse (antisense) orientation with respect to the KTi3 promoter in pBS10. The plasmid pBS10 was digested with Bam HI and a 3.47 kb fragment, representing the KTi3 promoter/antisense desaturase cDNA/KTi3 3' end transcriptional unit was isolated by agarose gel electrophoresis. The vector pML18 consists of the non-tissue specific and constitutive cauliflower mosaic virus (35S) promoter (Odell et al., (1985) *Nature* 313:810-812; Hull et al., (1987) *Virology* 86:482-493), driving expression of the neomycin phosphotransferase gene (Beck et al. (1982) *Gene* 19:327-336) followed by the 3' end of the nopaline synthase gene including nucleotides 848 to 1550 (Depicker et al. (1982) *J. Appl. Genet.* 1:561-574). This transcriptional unit was inserted into the commercial cloning vector pGEM9z (Gibco-BRL) and is flanked at the 5' end of the 35S promoter by the restriction sites Sal I, Xba I, Bam HI and Sma I in that order. An additional Sal I site is present at the 3' end of the NOS 3' sequence and the Xba I, Bam HI and Sal I sites are unique. The 3.47 kb transcriptional unit released from pBS10 was ligated into the Bam HI site of the vector pML18. When the resulting plasmids were digested with Sma I and Kpn I, plasmids containing inserts in the desired orientation yielded 3 fragments of 5.74, 2.69 and 1.46 kb. A plasmid with the transcriptional unit in the correct orientation was selected and was designated pBS13.

Figure 6:
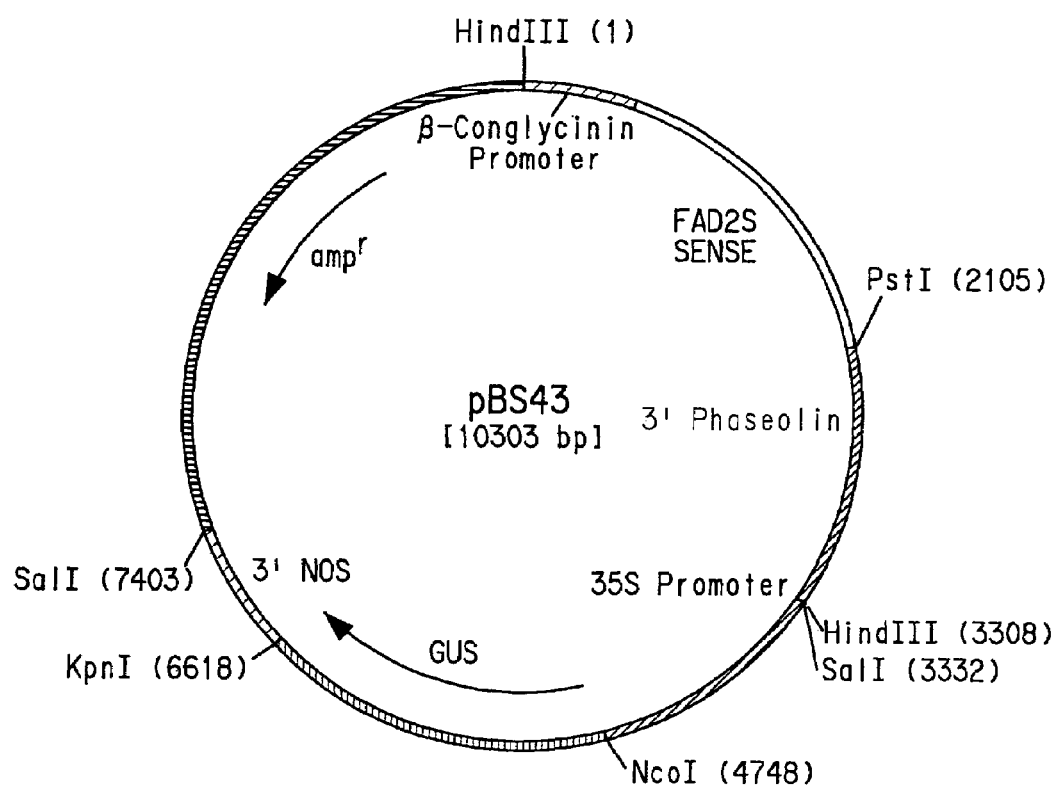
FIG. 6 is a restriction map of plasmid pBS43. This plasmid comprises a nucleic acid sequence encoding the *Glycine max* microsomal delta-12 desaturase under the transcriptional control of the soybean α-conglycinin promoter.

The 1.46 kb XbaI/EcoRV fragment from pBS13 (described above) was directionally cloned into the SmaI/XbaI site of vector pCST2 (described above) to yield a plasmid designated pBS39. The 3.3 kb HindIII fragment of plasmid pBS39 was cloned into the HindIII site of plasmid pMH40 (described above) to give the plant expression vector pBS43 (FIG. 6).

Transformation of Soybeans with Vector pBS43 and Identification of a Transgenic "Transwitch" Line The vector pBS43 was transformed into soybean meristems using the method of particle bombardment of soybean meristems (Christou et al (1990) *Trends Biotechnol.* 8:145-151). Seeds of transformed plants (i.e., from plants which had been identified as positive for GUS activity) were screened for fatty acid composition. Fatty acid methyl esters were prepared from hexane extracts of small (approx. 10 mg) seed chips (Browse et al (1986) *Anal. Biochem.* 152: 141-145). Seed chips from ten different transgenic lines were analysed and some of the R1 seeds from one of these lines, designated 260-05, had a total oleic acid content of 80-85% compared with about 20% in control seeds. This phenotype is caused by the cosuppression of the endogenous Fad 2-1 gene and is the result of the insertion of two copies of pBS43 into a locus of the soybean genome designated the "Transwitch locus" (Kinney, A. J. (1995) in "Induced Mutations and Molecular Techniques for Crop Improvement", International Atomic Energy Agency, Vienna). High oleic acid R1 seeds from line 260-05, which contained the Transwitch locus, were selfed and R2 seeds which were homozygous for the Transwitch locus were selected. Two of these R2 homozygous seeds (G94-1, G94-19) and seeds derived from further generations of G94-1 and G94-19 (R3, R4, R5), were selected for further analysis.

Figure 7:
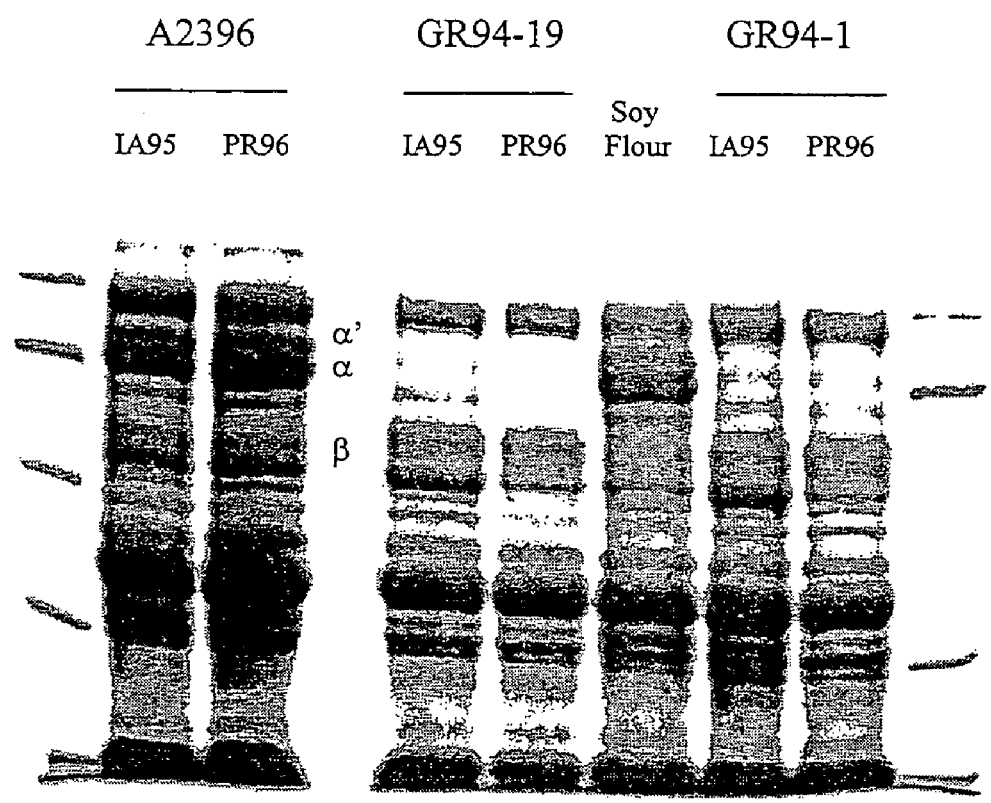
FIG. 7 is an SDS-PAGE gel of extracted protein from soybean seeds obtained from plants transformed with pBS43.

R5 seeds of G94-1 and G94-19 plants grown in both Iowa and Puerto Rico were ground into a powder and approximately 1 g extracted with 5 mL of hexane. After centrifugation, the hexane was poured off and the flakes allowed to air dry. Approximately 10 mg of defatted powder was extracted as described above and analyzed by SDS-PAGE. In both transgenic lines derived from both locations, the expression of the α' and α subunits of β-conglycinin were suppressed relative to control soybean lines and a standard soy flour (FIG. 7).

Example 3

To test if β-conglycinin expression could be suppressed using antisense technology, full length cDNAs of α and α' were made using reverse transcriptase polymerase chain reaction as described above. The upper primer, ConSa, is homologous to region 4-19 of both α and α' cDNA sequences with additional nucleotides added to the 5' end to code for a Kpn I restriction site. The lower primer used, Con1.9a, is homologous to regions 1818-1801 of SEQ ID NO:1, representing the α isoform, and 1920-1903 of SEQ ID NO:2, representing the α' isoform, respectively. To aid in subsequent cloning steps, additional nucleotides were added to the 5' end to code for an Nco I restriction site.

```
ConSa
5'-ACGGTACCGATGAGAGCGCGGTTCC-3'         (SEQ ID NO:8)
     Kpn I

Con1.9a
5'-AACCCATGGTCAGTAAAAAGCCCTCAA-3'       (SEQ ID NO:9)
     Nco I
```

Reverse transcription and subsequent PCR reaction were carried out as described above. RNA isolated from developing soybean seeds was reverse-transcribed using either random hexamers or Con1.9a (method as detailed above). The cDNA was amplified in a PCR reaction using ConSa and Con1.9a using the protocol detailed above. Fifteen microliters of the PCR reaction mixes were analyzed by agarose gel electrophoresis. A 1.8 kb band, the expected molecular weight for α, was observed. The remaining reaction mixes were purified using Wizard™ PCR Preps DNA Purification System kit (Promega). The α cDNA, which because of the primers used included a Kpn I site on the 5' end and an Nco I site on the 3' end, was digested with Nco I and Kpn I restriction enzymes. The resulting α cDNA was gel isolated, labeled as F10, and directionally cloned (antisense orientation) into pCW109 using the Nco I and Kpn I sites present in the plasmid. F10 was confirmed as α by PCR using nested primers (upper: Con.09 (SEQ ID NO:6); lower: Con1.4a (SEQ ID NO:5) and Con1.0 (SEQ ID NO:10)).

```
Con1.0   5'-CGGGTATGGCGAGTGTT-3'        (SEQ ID NO:10)
```

Figure 8:
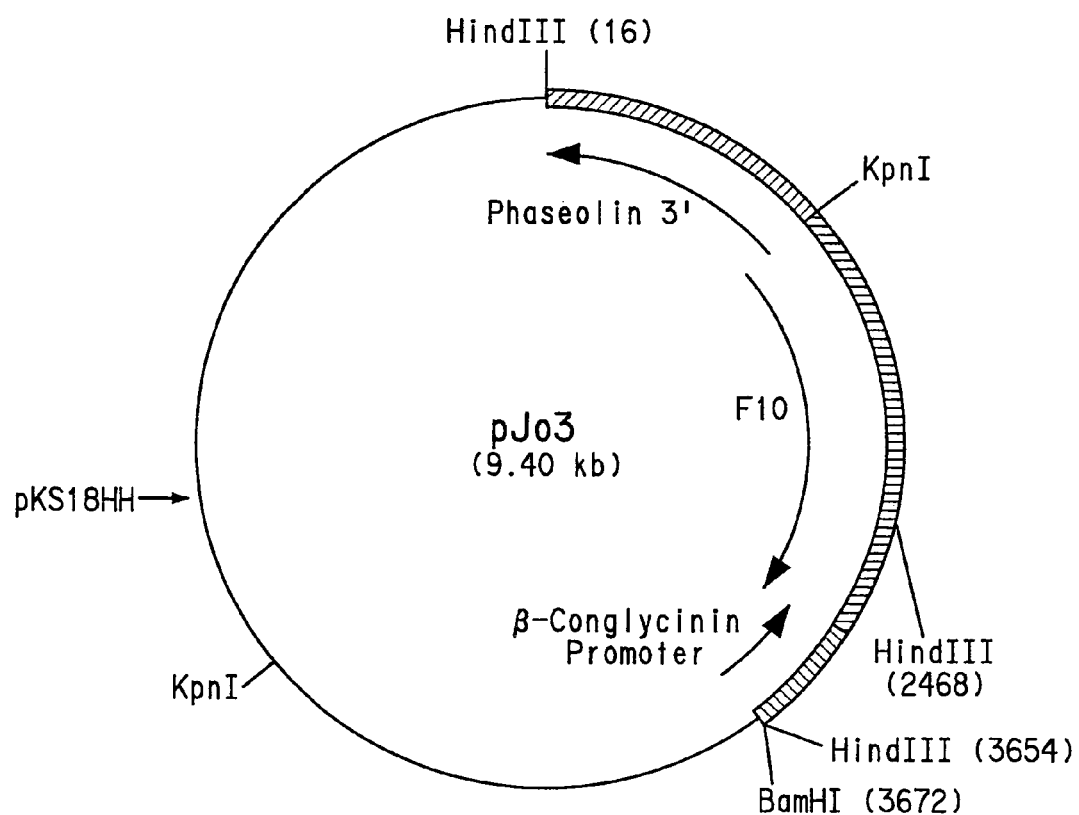
FIG. 8 is a restriction map of plasmid pJo3. This plasmid was derived by cloning the plant transcriptional unit KTi promoter/full length cDNA of the α subunit of β-conglycinin/KTi 3' end into the HindIII site of pKS18HH.

The transcriptional unit β-conglycinin promoter/α cDNA antisense/phaseolin 3' end was released from pCW109/F10 by partial digest with Hind III. Conditions of the partial digest were such that 6 fragments were produced (5.1 kb, 3.8 kb, 3.6 kb, 2.6 kb, 2.4 kb, and 1.2 kb). The 3.6 kb fragment containing the the transcriptional unit was gel isolated and labeled F14. F14 was then cloned into the Hind III site of pKS18HH. After confirming insertion by digestion of plasmid DNA preparations made from tansformed cells with Hind III, the plasmid DNA from positive cultures was digested with Kpn I to ensure that they contained the 3.6 kb F14 fragment and not the 3.8 kb fragment from the partial digest of pCW109/F10 with Hind III. F14 contains a Kpn I site, while the 3.8 kb fragment does not. Upon confirmation, pKS18HH/F14 was labeled pJo3 (FIG. 8). Soybean embryonic suspension cultures were transformed with pJo3 as detailed above. Transformation resulted in 5 transformed clones; upon maturation each clone gave rise to 4 to 8 somatic embryos.

Protein extracts of transformed somatic embryos were analyzed by SDS-PAGE as previously detailed. Results are presented in Table 2. The transgenic clones all gave rise to at least one somatic embryo in which the expression of both α and α' was suppressed.

TABLE 2

| Clone | Embryo | α | α' | β |
|---|---|---|---|---|
| Jo3-1 | 1 | − | − | + |
|  | 2 | + | + | + |
| Jo3-2 | 1 | − | − | + |
|  | 2 | − | − | + |
| Jo3-2b | 1 | − | − | + |
|  | 2 | − | − | + |

TABLE 2-continued

| Clone | Embryo | α | α' | β |
|---|---|---|---|---|
| Jo3-3 | 1 | − | − | + |
|  | 2 | − | − | + |
| Jo3-4 | 1 | − | − | + |
|  | 2 | − | − | + |

Example 4

There are five non allelic genes that code for the glycinin subunits. Sequencing genomic clones and cDNA's have lead to a division of the subunit genes into two groups based on sequence similarity. Group I consists of Gy1 (SEQ ID NO:11), Gy2 (SEQ ID NO:12) and Gy3 (SEQ ID NO:13), whereas group II consists of Gy4 (SEQ ID NO:14) and Gy5 (SEQ ID NO:15). There is greater than 85% similarity between genes within a group, but only 42% to 46% similarity between genes of different groups. To determine whether expression of glycinin can be suppressed in developing cotyledons by employing co-suppression technology, cDNA's of Group I and Group II were prepared using reverse transcriptase polymerase chain reaction as described above.

The upper primer used for Group I reactions (G1-1) is homologus to regions 1-19 for all Group I cDNA's. Two lower primers were used: G1-1039, which is homologous with regions 1038-1022 of Gy1, 1008-992 of Gy2, and 996-980 of Gy3; or G1-1475, which is homologus to regions 1475-1460 of Gy1, 1445-1430 of Gy2 and 1433-1418 of Gy3. To aid in future cloning, all primers contained additional nucleotides that coded for a Not I restriction site at their 5' end.

```
G1-1
5'-GCGGCCGCATGGCCAAGCTAGTTTTTT-3'     (SEQ ID NO:16)
    Not I

G1-1039
5'-GCGGCCGCTGGTGGCGTTTGTGA-3'         (SEQ ID NO:17)
    Not I

G1-1475
5'-GCGGCCGCTCTTCTGAGACTCCT-3'         (SEQ ID NO:18)
    Not I
```

RNA isolated from developing soybean seeds was reverse-transcribed using either random hexamers, or G1-1475 or G1-1039 as the lower primer in the reactions. cDNA fragments were amplified using a mixture of G1-1 with either G1-1039 or G1-1475. Fifteen microliters of the PCR reaction mixes were analyzed by agarose gel electrophoresis. PCR reactions resulted in products of the expected molecular weight, approximately 1 kb and 1.4-1.5 kb for primer sets G1-1/G1-1039 and G1-1/G1-1475, respectively. cDNA fragments from the remainder of the reaction mixes were purified using the Wizard™ PCR Preps DNA Purification System kit (Promega). Purified cDNA's were then digested with Not I and isolated by agarose gel purification.

The upper primer used for RT-PCR reactions of Group II (G4-7) is homologus to regions 7-22 for both cDNA's of Group II. Two lower primers were used: G4-1251 which is homologus with regions 1251-1234 of Gy4 and 1153-1135 of Gy5; or G4-1670 which is homologus to regions 1668-1653 of Gy4. There is no similar region in Gy5. To aid in future cloning all primers contained additional nucleotides that coded for a Not I restriction site at their 5' end.

```
G4-7
5'-GCGGCCGCATGCCCTTCACTCTCT-3'        (SEQ ID NO:19)
    Not I

G4-1251
5'-GCGGCCGCTGGGAGGGTGAGGCTGTT-3'      (SEQ ID NO:20)
    Not I

G4-1670
5'-GCGGCCGCTGAGCCTTGTTGAGAC-3'        (SEQ ID NO:21)
    Not I
```

RNA isolated from developing soybean seeds was reverse-transcribed using either random hexamers, or G4-1251 or G4-1670 as the lower primer in the reactions. cDNA fragments were amplified using a mixture of G4-7 with either G4-1251 or G4-1670. Fifteen microliters of the PCR reaction mixes were analyzed by agarose gel electrophoresis. PCR reactions resulted in products of the expected molecular weight, approximately 1.25 kb and 1.7 kb for primer sets G4-7/G4-1251 and G4-7/G4-16.70, respectively. cDNA fragments from the remainder of the reaction mixes were purified using the Wizard™ PCR Preps DNA Purification System kit (Promega). Purified cDNA's were then digested with Not I and isolated from gels.

Figure 9:
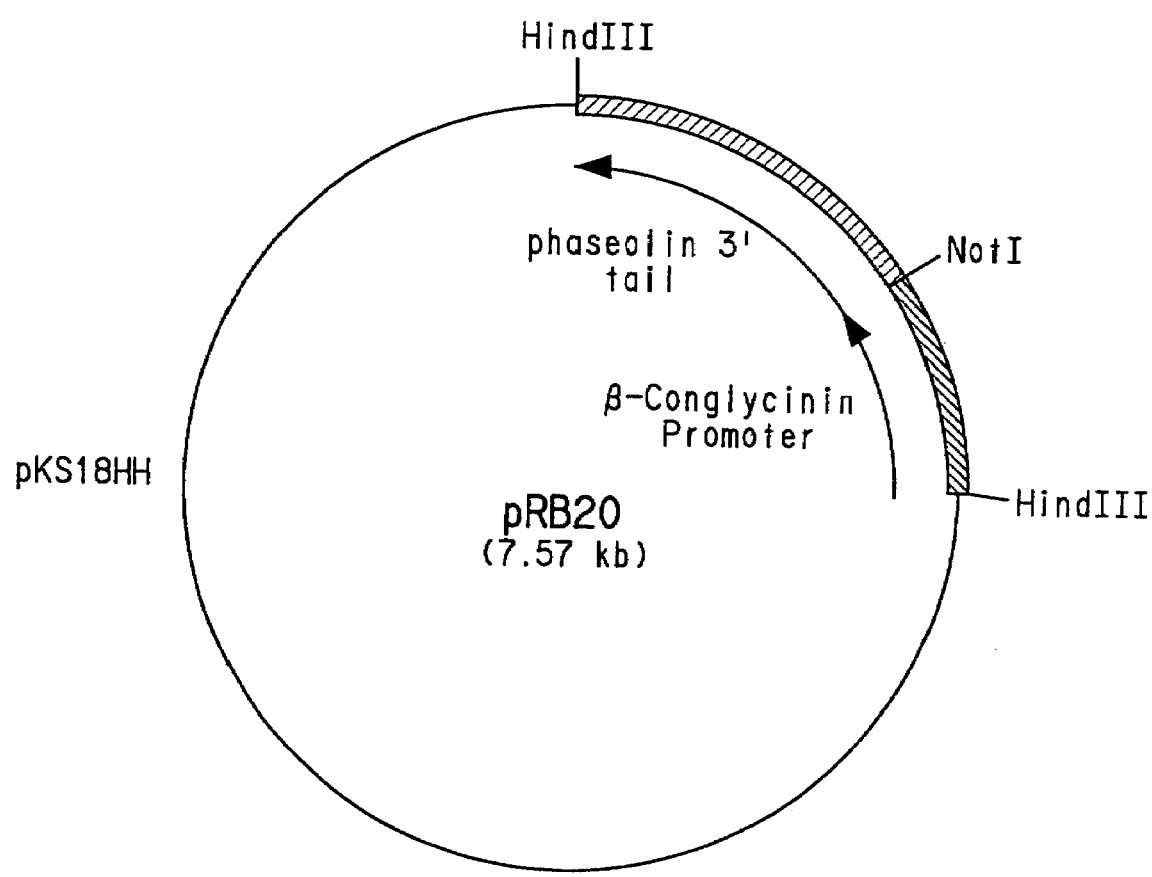
FIG. 9 is a restriction map of plasmid pRB20. This plasmid was derived by cloning the transcriptional unit β-conglycinin promoter/Phaseolin 3' end into the HindIII site of pKS18HH. It is used as an intermediate cloning vehicle in construction of chimeric genes of the instant invention.

The isolated group I cDNAs are cloned into pRB20 (FIG. 9) at the Not I site (sense oritentation). After partial restriction digest with Not I and isolation of the single cut pRB20/group I linear fragments, group II cDNA are added to create final transcriptional units β-conglycinin promoter/group I cDNA (sense orientation)/phaseolin 3' end and β-conglycinin promoter/group II cDNA (sense orientation)/phaseolin 3' end. The resulting plasmids are then used to transform somatic embryonic suspension cultures using the method detailed above.

The invention claimed is:

1. Feed prepared from soybean seeds prepared by a method for simultaneously reducing the expression of two soybean genes comprising:
   (a) constructing a chimeric gene comprising:
      (i) a nucleic acid fragment encoding a promoter region from a soybean seed storage protein gene; and
      (ii) a nucleic acid fragment encoding all or a portion of a soybean protein that is not the soybean seed storage protein of (i), said nucleic acid fragment placed in sense or antisense orientation relative to the promoter of (i), and (iii) a transcriptional termination region;
   (b) creating a transgenic soybean seed by introducing into a soybean seed the chimeric gene of (a); and
   (c) growing the transgenic soybean seeds of step (b) under conditions that result in expression of the chimeric gene of step (a)

wherein the quantity of one or more members of a class of soybean seed storage protein subunits and the quantity of the protein encoded by the nucleic acid fragment of (a)(ii) is reduced when compared to soybeans not comprising the chimeric gene of step (a) and wherein the class of soybean seed storage protein subunits is selected from the group consisting of: glycinin and β-conglycinin.

* * * * *

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 1818 base pairs
      (B) TYPE: nucleic acid
      (C) STRANDEDNESS: single (D) TOPOLOGY: linear (ii) MOLECULE TYPE: cDNA (xi) SEQUENCE DESCRIPTION: SEQ ID NO: 1:

| | |
|---|---|
| ATGATGAGAG CACGGTTCCC ATTACTGTTG CTGGGACTTG TTTTCCTGGC TTCAGTTTCT | 60 |
| GTCTCATTTG GCATTGCTTA CTGGGAAAAA GAGAACCCCA AACACAACAA GTGTCTCCA | 120 |
| AGTTGCAATA GCGAGAGAGA CTCGTACAGG AACCAAGCAT GCCACGCTCG TTGCAACCT | 180 |
| CTTAAGGTGG AGAAAGAAGA ATGTGAAGAA GGTGAAATTC CACGACCACG ACCACGACC | 240 |
| CAACACCCGG AGAGGGAACC TCAGCAACCC GGTGAGAAGG AGGAAGACGA AGATGAGCA | 300 |
| CCACGTCCAA TCCCATTCCC ACGCCCACAA CCTCGTCAAG AAGAAGAGCA CGAGCAGAG | 360 |
| GAGGAACAGG AATGGCCTCG CAAGGAGGAA AAACGCGGAG AAAAGGGAAG TGAAGAGGA | 420 |
| GATGAGGATG AGGATGAGGA ACAAGATGAA CGTCAATTCC CATTCCCACG CCCACCTCA | 480 |
| CAGAAGGAAG AGCGAAACGA AGAGGAAGAT GAGGATGAGG AGCAGCAGCG AGAGAGCGA | 540 |
| GAAAGTGAAG ATTCTGAGTT ACGAAGACAT AAGAATAAGA ACCCTTTTCT CTTCGGCTC | 600 |
| AACAGGTTCG AAACTCTCTT CAAAAACCAA TATGGTCGCA TTCGCGTCCT CCAGAGGTT | 660 |
| AACCAACGCT CCCCACAACT TCAGAATCTC CGAGACTACC GCATTTTGGA GTTCAACTC | 720 |
| AAACCCAACA CCCTCCTTCT CCCCAACCAT GCTGACGCTG ATTACCTCAT CGTTATCCT | 780 |
| AACGGGACTG CCATTCTTTC CTTGGTGAAC AACGACGACA GAGACTCCTA CAGACTTCA | 840 |
| TCTGGTGATG CCCTGAGAGT CCCCTCAGGA ACCACATACT ATGTGGTCAA CCCTGACAA | 900 |
| AACGAAAATC TCAGATTAAT AACACTCGCC ATACCCGTTA ACAAGCCTGG TAGATTTGA | 960 |
| AGTTTCTTCC TATCTAGCAC TGAAGCTCAA CAATCCTACT TGCAAGGATT CAGCAGGA | 1020 |
| ATTTTAGAGG CCTCCTACGA TACCAAATTC GAGGAGATAA ACAAGGTTCT GTTTAGTA | 1080 |
| GAGGAAGGGC AGCAGCAAGG GGAGCAGAGG CTGCAAGAGA GCGTGATTGT GGAAATCT | 1140 |
| AAGGAACAGA TTCGGGCACT GAGCAAACGT GCCAAATCTA GTTCAAGGAA AACCATTT | 1200 |
| TCTGAAGATA AACCTTTTAA CTTGAGAAGC CGCGACCCCA TCTACTCCAA CAAGCTTG | 1260 |
| AAGTTCTTTG AGATCACCCC AGAGAAAAAC CCCCAGCTTC GGGACTTGGA TATCTTCC | 1320 |
| AGTATTGTGG ATATGAACGA GGGAGCTCTT CTTCTACCAC ACTTCAATTC AAAGGCGA | 1380 |
| GTGATACTGG TAATTAATGA AGGAGATGCA AACATTGAAC TTGTTGGCCT AAAAGAAC | 1440 |
| CAACAGGAGC AGCAACAGGA AGAGCAACCT TTGGAAGTGC GGAAATATAG AGCCGAAT | 1500 |
| TCTGAACAAG ATATATTTGT AATCCCAGCA GGTTATCCAG TTGTGGTCAA CGCTACCT | 1560 |
| AATCTGAATT TCTTTGCTAT TGGTATTAAT GCCGAGAACA ACCAGAGGAA CTTCCTCG | 1620 |
| GGTTCGCAAG ACAATGTGAT AAGCCAGATA CCTAGTCAAG TGCAGGAGCT TGCATTCC | 1680 |
| GGGTCTGCAC AAGCTGTTGA GAAGCTATTA AAGAACCAAA GAGAATCCTA CTTTGTGG | 1740 |
| GCTCAGCCTA AGAAGAAAGA GGAGGGGAAT AAGGGAAGAA AGGGTCCTTT GTCTTCAA | 1800 |
| TTGAGGGCTT TTTACTGA | 1818 |

(2) INFORMATION FOR SEQ ID NO: 2:

(i) SEQUENCE CHARACTERISTICS:
        (A) LENGTH: 1920 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

```
ATGATGAGAG CGCGGTTCCC ATTACTGTTG CTGGGAGTTG TTTTCCTAGC ATCAGTTTCT      60
GTCTCATTTG GCATTGCGTA TTGGGAAAAG CAGAACCCCA GTCACAACAA GTGCCTCCG      120
AGTTGCAATA GCGAGAAAGA CTCCTACAGG AACCAAGCAT GCCACGCTCG TTGCAACCT      180
CTTAAGGTGG AGGAAGAAGA AGAATGCGAA GAAGGTCAAA TTCCACGACC ACGACCACA      240
CACCCGGAGA GGGAACGTCA GCAACACGGT GAGAAGGAGG AAGACGAAGG TGAGCAGCC      300
CGTCCATTCC CATTCCCACG CCCACGCCAA CCTCATCAAG AGGAAGAGCA CGAGCAGAA      360
GAGGAACACG AATGGCATCG CAAGGAGGAA AAACACGGAG GAAAGGGAAG TGAAGAGGA      420
CAAGATGAAC GTGAACACCC ACGCCCACAC CAACCTCATC AAAAGGAAGA GGAAAAGCA      480
GAATGGCAAC ACAAGCAGGA AAAGCACCAA GGAAAGGAAA GTGAAGAAGA AGAAGAAGA      540
CAAGACGAGG ATGAGGAGCA AGACAAAGAG AGCCAAGAAA GTGAAGGTTC TGAGTCTCA      600
AGAGAACCAC GAAGACATAA GAATAAGAAC CCTTTTCACT TCAACTCTAA AAGGTTCCA      660
ACTCTCTTCA AAAACCAATA TGGCCACGTT CGCGTCCTCC AGAGGTTCAA CAAACGCTC      720
CAACAGCTTC AGAATCTCCG AGACTACCGC ATTTTGGAGT TCAACTCCAA ACCCAACAC      780
CTTCTTCTCC CCCACCATGC TGACGCTGAT TACCTCATCG TTATCCTTAA CGGGACTGC      840
ATTCTTACCT TGGTGAACAA CGACGACCGA GACTCTTACA ACCTTCAATC TGGCGATGC      900
CTAAGAGTCC CTGCAGGAAC CACATTCTAT GTGGTTAACC CTGACAACGA CGAGAATCT      960
AGAATGATAG CAGGAACCAC ATTCTATGTG GTTAACCCTG ACAACGACGA GAATCTCA     1020
ATGATAACAC TCGCCATACC CGTTAACAAA CCCGGTAGAT TTGAGAGTTT CTTCCTAT     1080
AGCACTCAAG CTCAACAGTC CTACTTGCAA GGGTTCAGCA AGAATATTCT AGAGGCCT     1140
TACGACACCA AATTCGAGGA GATAAACAAG GTTCTGTTTG GTAGAGAGGA GGGGCAGC     1200
CAAGGGGAGG AGAGGCTGCA AGAGAGTGTG ATTGTGGAAA TCTCAAAGAA ACAAATTC     1260
GAACTGAGCA AACATGCCAA ATCTAGTTCA AGGAAAACCA TTTCTTCTGA AGATAAAC     1320
TTCAACTTGG GAAGCCGCGA CCCCATCTAT TCCAACAAGC TTGGCAAGTT GTTTGAGA     1380
ACCCAGAGAA ACCCTCAGCT TCGGGACTTG GATGTCTTCC TCAGTGTTGT GGATATGA     1440
GAGGGAGCTC TTTTTCTACC ACACTTCAAT TCAAAGGCCA TAGTGGTACT AGTGATTA     1500
GAAGGAGAAG CAAACATTGA ACTTGTTGGC ATTAAAGAAC AACAACAGAG GCAGCAAC     1560
GAAGAGCAAC CTTTGGAAGT GCGGAAATAT AGAGCTGAAT TGTCTGAACA AGATATAT     1620
GTAATCCCAG CAGGTTATCC AGTTATGGTC AACGCTACCT CAGATCTGAA TTTCTTTG     1680
TTTGGTATCA ATGCCGAGAA CAACCAGAGG AACTTCCTTG CAGGTTCGAA AGACAATG     1740
ATAAGCCAGA TACCTAGTCA AGTGCAGGAG CTTGCGTTCC CTAGGTCTGC AAAAGATA     1800
GAGAACCTAA TAAAGAGCCA AAGTGAGTCC TACTTTGTGG ATGCTCAGCC TCAGCAGA     1860
GAGGAGGGGA ACAAGGGAAG AAAGGGTCCT TTGTCTTCAA TTTTGAGGGC TTTTTACT     1920
```

(2) INFORMATION FOR SEQ ID NO: 3:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

-continued

```
ATGATGAGAG TGCGGTTTCC TTTGTTGGTG TTGCTGGGAA CTGTTTTCCT GGCATCAGTT      60

TGTGTCTCAT TAAAGGTGAG AGAGGATGAG AATAACCCTT TCTACTTTAG AAGCTCTAA     120

AGCTTCCAAA CTCTCTTTGA GAACCAAAAC GTTCGCATTC GTCTCCTCCA GAGATTCAA     180

AAACGCTCCC CACAACTTGA GAACCTTCGA GACTACCGGA TTGTCCAGTT TCAGTCAAA     240

CCCAACACAA TCCTTCTCCC CCACCATGCT GACGCCGATT TCCTCCTCTT TGTCCTTAG     300

GGGAGAGCCA TACTTACCTT GGTGAACAAC GACGACAGAG ACTCCTACAA CCTTCACCC     360

GGCGATGCCC AGAGAATCCC AGCTGGAACC ACTTACTATT TGGTTAACCC TCACGACCA     420

CAGAATCTCA AAATAATCAA ACTTGCCATA CCCGTCAACA AACCTGGCAG ATATGATGA     480

TTCTTCTTAT CTAGCACTCA AGCCCAACAG TCCTACTTGC AAGGCTTCAG CCATAATAT     540

CTAGAGACCT CCTTCCATAG CGAATTCGAG GAGATAAACA GGGTTTTGTT TGGAGAGGA     600

GAGGAGCAGA GGCAGCAAGA GGGAGTGATC GTGGAACTCT CAAAGGAACA AATTCGGCA     660

CTGAGCAGAC GTGCCAAATC TAGTTCAAGG AAAACCATTT CCTCCGAAGA TGAACCATT     720

AACTTGAGAA GCCGCAACCC CATCTATTCC AACAACTTTG GAAAGTTCTT TGAGATCAC     780

CCTGAGAAAA ACCCACAGCT TCGGGACTTG GATATCTTCC TCAGTTCTGT GGATATCAA     840

GAAGGAGCTC TTCTTCTACC ACACTTCAAT TCAAAGGCCA TAGTGATACT AGTGATTAA     900

GAAGGAGATG CAAACATTGA ACTTGTTGGC ATTAAAGAAC AACAACAGAA GCAGAAACA     960

GAAGAGGAAC CTTTGGAAGT GCAAAGGTAC AGAGCTGAAT TGTCTGAAGA CGATGTAT    1020

GTAATTCCAG CAGCTTATCC ATTTGTCGTC AACGCTACCT CAAACCTCAA TTTCCTTG    1080

TTTGGTATCA ATGCTGAGAA CAACCAGAGG AACTTCCTTG CAGGCGAGAA AGACAATG    1140

GTAAGGCAGA TAGAAAGACA AGTGCAGGAG CTTGCGTTCC CTGGGTCTGC ACAAGATG    1200

GAGAGGCTAT TAAAGAAGCA GAGGGAATCC TACTTTGTTG ATGCTCAGCC TCAGCAGA    1260

GAGGAGGGGA GTAAGGGAAG AAAGGGTCCT TTTCCTTCAA TCTTAGGTGC TCTCTACT    1320
```

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
CGTACCATGG TGAGAGCGCG GTTCC                                          25
```

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
CGGTACCGAA TTGAAGTGTG GTAG                                           24
```

(2) INFORMATION FOR SEQ ID NO: 6:

(i) SEQUENCE CHARACTERISTICS:
        (A) LENGTH: 27 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

TCGTCCATGG AGCGCGGTTC CCATTAC                                              27

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

TCTCGGTCGT CGTTGTT                                                         17

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

ACGGTACCGA TGAGAGCGCG GTTCC                                                25

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

AACCCATGGT CAGTAAAAAG CCCTCAA                                              27

(2) INFORMATION FOR SEQ ID NO: 10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CGGGTATGGC GAGTGTT                                                         17

(2) INFORMATION FOR SEQ ID NO: 11:

(i) SEQUENCE CHARACTERISTICS:
        (A) LENGTH: 1488 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO: 11:

| | |
|---|---|
| ATGGCCAAGC TAGTTTTTTC CCTTTGTTTT CTGCTTTTCA GTGGCTGCTG CTTCGCTTTC | 60 |
| AGTTCCAGAG AGCAGCCTCA GCAAAACGAG TGCCAGATCC AAAAACTCAA TGCCCTCAA | 120 |
| CCGGATAACC GTATAGAGTC AGAAGGAGGG CTCATTGAGA CATGGAACCC TAACAACAA | 180 |
| CCATTCCAGT GTGCCGGTGT TGCCCTCTCT CGCTGCACCC TCAACCGCAA CGCCCTTCG | 240 |
| AGACCTTCCT ACACCAACGG TCCCCAGGAA ATCTACATCC AACAAGGTAA GGGTATTTT | 300 |
| GGCATGATAT ACCCGGGTTG TCCTAGCACA TTTGAAGAGC CTCAACAACC TCAACAAAG | 360 |
| GGACAAAGCA GCAGACCACA GACCGTCAC CAGAAGATCT ATAACTTCAG AGAGGGTGA | 420 |
| TTGATCGCAG TGCCTACTGG TGTTGCATGG TGGATGTACA ACAATGAAGA CACTCCTGT | 480 |
| GTTGCCGTTT CTATTATTGA CACCAACAGC TTGGAGAACC AGCTCGACCA GATGCCTAG | 540 |
| AGATTCTATC TTGCTGGGAA CCAAGAGCAA GAGTTTCTAA AATATCAGCA AGAGCAAGG | 600 |
| GGTCATCAAA GCCAGAAAGG AAAGCATCAG CAAGAAGAAG AAAACGAAGG AGGCAGCAT | 660 |
| TTGAGTGGCT TCACCCTGGA ATTCTTGGAA CATGCATTCA GCGTGGACAA GCAGATAGC | 720 |
| AAAAACCTAC AAGGAGAGAA CGAAGGGGAA GACAAGGGAG CCATTGTGAC AGTGAAAGG | 780 |
| GGTCTGAGCG TGATAAAACC ACCCACGGAC GAGCAGCAAC AAAGACCCCA GGAAGAGGA | 840 |
| GAAGAAGAAG AGGATGAGAA GCCACAGTGC AAGGGTAAAG ACAAACACTG CCAACGCCC | 900 |
| CGAGGAAGCC AAAGCAAAAG CAGAAGAAAT GGCATTGACG AGACCATATG CACCATGAG | 960 |
| CTTCGCCACA ACATTGGCCA GACTTCATCA CCTGACATCT ACAACCCTCA AGCCGGTA | 1020 |
| GTCACAACCG CCACCAGCCT TGACTTCCCA GCCCTCTCGT GGCTCAGACT CAGTGCTG | 1080 |
| TTTGGATCTC TCCGCAAGAA TGCAATGTTC GTGCCACACT ACAACCTGAA CGCGAACA | 1140 |
| ATAATATACG CATTGAATGG ACGGGCATTG ATACAAGTGG TGAATTGCAA CGGTGAGA | 1200 |
| GTGTTTGATG GAGAGCTGCA AGAGGGACGG GTGCTGATCG TGCCACAAAA CTTTGTGG | 1260 |
| GCTGCAAGAT CACAGAGTGA CAACTTCGAG TATGTGTCAT TCAAGACCAA TGATACAC | 1320 |
| ATGATCGGCA CTCTTGCAGG GGCAAACTCA TTGTTGAACG CATTACCAGA GGAAGTGA | 1380 |
| CAGCACACTT TCAACCTAAA AAGCCAGCAG GCCAGGCAGA TAAAGAACAA CAACCCTT | 1440 |
| AAGTTCCTGG TTCCACCTCA GGAGTCTCAG AAGAGAGCTG TGGCTTAG | 1488 |

(2) INFORMATION FOR SEQ ID NO: 12:

(i) SEQUENCE CHARACTERISTICS:
        (A) LENGTH: 1458 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

| | |
|---|---|
| ATGGCCAAGC TTGTTCTTTC CCTTTGTTTC CTTCTTTTCA GTGGCTGCTT CGCTCTGAGA | 60 |
| GAGCAGGCAC AGCAAAATGA GTGCCAGATC CAAAAGCTGA ATGCCCTCAA ACCGGATAA | 120 |
| CGTATAGAGT CGGAAGGTGG GTTCATTGAG ACATGGAACC CTAACAACAA GCCATTCCA | 180 |
| TGTGCCGGTG TTGCCCTCTC TCGCTGCACC CTTAACCGCA ATGCCCTTCG TAGACCTTC | 240 |
| TACACCAACG GTCCCCAGGA AATCTACATA CAACAAGGTA ATGGTATTTT TGGCATGAT | 300 |
| TTCCCGGGTT GTCCTAGCAC TTATCAAGAG CCGCAAGAAT CTCAGCAACG AGGACGAAG | 360 |

-continued

| | |
|---|---|
| CAGAGGCCCC AAGACCGTCA CCAAAAGGTA CATCGCTTCA GAGAGGGTGA TTTGATCGC | 420 |
| GTGCCTACTG GTGTTGCATG GTGGATGTAC AACAATGAAG ACACTCCTGT TGTTGCCGT | 480 |
| TCTATTATTG ACACCAACAG CTTGGAGAAC CAGCTCGACC AGATGCCTAG GAGATTCTA | 540 |
| CTTGCTGGGA ACCAAGAGCA AGAGTTTCTA AAATATCAGC AGCAGCAGCA AGGAGGTTC | 600 |
| CAAAGCCAGA AAGGAAAGCA ACAAGAAGAA GAAAACGAAG GAAGCAACAT ATTGAGTGG | 660 |
| TTCGCCCCTG AATTCTTGAA AGAAGCGTTC GGCGTGAACA TGCAGATAGT GAGAAACCT | 720 |
| CAAGGTGAGA ACGAAGAGGA GGATAGTGGA GCCATTGTGA CAGTGAAAGG AGGTCTAAG | 780 |
| GTCACAGCTC CAGCCATGAG GAAGCCACAG CAAGAAGAAG ATGATGATGA TGAGGAAGA | 840 |
| CAGCCACAGT GCGTGGAGAC AGACAAAGGT TGCCAACGCC AAAGCAAAAG GAGCAGAAA | 900 |
| GGCATTGATG AGACCATTTG CACAATGAGA CTTCGCCAAA ACATTGGTCA GAATTCATC | 960 |
| CCTGACATCT ACAACCCTCA AGCTGGTAGC ATCACAACCG CCACCAGCCT TGACTTCC | 1020 |
| GCCCTCTGGC TTCTCAAACT CAGTGCCCAG TATGGATCAC TCCGCAAGAA TGCTATGT | 1080 |
| GTGCCACACT ACACCCTGAA CGCGAACAGC ATAATATACG CATTGAATGG GCGGGCAT | 1140 |
| GTACAAGTGG TGAATTGCAA TGGTGAGAGA GTGTTTGATG GAGAGCTGCA AGAGGGAG | 1200 |
| GTGCTGATCG TTCCACAAAA CTTTGCGGTG GCTGCAAAAT CCCAGAGCGA TAACTTTG | 1260 |
| TATGTGTCAT TCAAGACCAA TGATAGACCC TCGATCGGAA ACCTTGCAGG GGCAAACT | 1320 |
| TTGTTGAACG CATTGCCAGA GGAAGTGATT CAGCACACTT TTAACCTAAA GAGCCAGC | 1380 |
| GCCAGGCAGG TGAAGAACAA CAACCCTTTC AGCTTCCTTG TTCCACCTCA GGAGTCTC | 1440 |
| AGGAGAGCTG TGGCTTAG | 1458 |

(2) INFORMATION FOR SEQ ID NO: 13:

(i) SEQUENCE CHARACTERISTICS:
        (A) LENGTH: 1446 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

| | |
|---|---|
| ATGGCTAAGC TTGTTCTTTC CCTTTGTTTT CTGCTTTTCA GTGGCTGCTG CTTCGCTTTC | 60 |
| AGTTTCAGAG AGCAGCCACA GCAAAACGAG TGCCAGATCC AACGCCTCAA TGCCCTAAA | 120 |
| CCGGATAACC GTATAGAGTC AGAAGGTGGC TTCATTGAGA CATGGAACCC TAACAACAA | 180 |
| CCATTCCAGT GTGCCGGTGT TGCCCTCTCT CGCTGCACCC TCAACCGCAA CGCCCTTCG | 240 |
| AGACCTTCCT ACACCAACGC TCCCCAGGAG ATCTACATCC AACAAGGTAG TGGTATTTT | 300 |
| GGCATGATAT TCCCGGGTTG TCCTAGCACA TTTGAAGAGC CTCAACAAAA AGGACAAAG | 360 |
| AGCAGGCCCC AAGACCGTCA CCAGAAGATC TATCACTTCA GAGAGGGTGA TTTGATTGC | 420 |
| GTGCCAACCG GTTTTGCATA CTGGATGTAC AACAATGAAG ACACTCCTGT TGTTGCCGT | 480 |
| TCTCTTATTG ACACCAACAG CTTCCAGAAC CAGCTCGACC AGATGCCTAG GAGATTCTA | 540 |
| CTTGCTGGGA ACCAAGAGCA AGAGTTTCTA CAGTATCAGC CACAGAAGCA GCAAGGAGG | 600 |
| ACTCAAAGCC AGAAAGGAAA GCGTCAGCAA GAAGAAGAAA ACGAAGGAGG CAGCATATT | 660 |
| AGTGGCTTCG CCCCGGAATT CTTGGAACAT GCGTTCGTCG TGGACAGGCA GATAGTGAG | 720 |
| AAGCTACAAG GTGAGAACGA AGAGGAAGAG AAGGGTGCCA TTGTGACAGT GAAAGGAGG | 780 |
| CTCAGCGTGA TAAGCCCACC CACGGAAGAG CAGCAACAAA GACCCGAGGA AGAGGAGAA | 840 |

| | |
|---|---|
| CCAGATTGTG ACGAGAAAGA CAAACATTGC CAAAGCCAAA GCAGAAATGG CATTGACGA | 900 |
| ACCATTTGCA CAATGAGACT TCGCCACAAC ATTGGCCAGA CTTCATCACC TGACATCTT | 960 |
| AACCCTCAAG CTGGTAGCAT CACAACCGCT ACCAGCCTCG ACTTCCCAGC CCTCTCGT | 1020 |
| CTCAAACTCA GTGCCCAGTT TGGATCACTC CGCAAGAATG CTATGTTCGT GCCACACT | 1080 |
| AACCTGAACG CAAACAGCAT AATATACGCA TTGAATGGAC GGGCATTGGT ACAAGTGG | 1140 |
| AATTGCAATG GTGAGAGAGT GTTTGATGGA GAGCTGCAAG AGGGACAGGT GTTAATTG | 1200 |
| CCACAAAACT TTGCGGTGGC TGCAAGATCA CAGAGCGACA ACTTCGAGTA TGTTTCAT | 1260 |
| AAGACCAATG ATAGACCCTC GATCGGCAAC CTTGCAGGTG CAAACTCATT GTTGAACG | 1320 |
| TTGCCGGAGG AAGTGATTCA GCAAACTTTT AACCTAAGGA GGCAGCAGGC CAGGCAGG | 1380 |
| AAGAACAACA ACCCTTTCAG CTTCCTGGTT CCACCTAAGG AGTCTCAGAG GAGAGTTG | 1440 |
| GCTTAG | 1446 |

(2) INFORMATION FOR SEQ ID NO: 14:

(i) SEQUENCE CHARACTERISTICS:
        (A) LENGTH: 1689 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

| | |
|---|---|
| ATGGGGAAGC CCTTCACTCT CTCTCTTTCT TCCCTTTGCT TGCTACTCTT GTCGAGTGCA | 60 |
| TGCTTTGCTA TTAGCTCCAG CAAGCTCAAC GAGTGCCAAC TCAACAACCT CAACGCGTT | 120 |
| GAACCCGACC ACCGCGTTGA GTTCGAAGGT GGTTTGATTC AAACATGGAA CTCTCAACA | 180 |
| CCTGAGCTGA AATGCGCCGG TGTCACTGTT TCCAAACTCA CCCTCAACCG CAATGGCCT | 240 |
| CACTTGCCAT CTTACTCACC TTATCCCCGG ATGATCATCA TCGCCCAAGG GAAAGGAGC | 300 |
| CTGCAGTGCA AGCCAGGATG TCCTGAGACG TTTGAGGAGC CACAAGAACA ATCAAACAG | 360 |
| AGAGGCTCAA GGTCGCAGAA GCAGCAGCTA CAGGACAGTC ACCAGAAGAT TCGTCACTT | 420 |
| AATGAAGGAG ACGTACTCGT GATTCCTCCT GGTGTTCCTT ACTGGACCTA TAACACTGG | 480 |
| GATGAACCAG TTGTTGCCAT CAGTCTTCTT GACACCTCTA ACTTCAATAA CCAGCTTGA | 540 |
| CAAACCCCTA GGGTATTTTA CCTTGCTGGG AACCCAGATA TAGAGTACCC AGAGACCAT | 600 |
| CAACAACAAC AACAGCAGAA AAGTCATGGT GGACGCAAGC AGGGGCAACA CCAGCAGGA | 660 |
| GAAGAGGAAG AAGGTGGCAG CGTGCTCAGT GGCTTCAGCA ACACTTCTT GGCACAATC | 720 |
| TTCAACACCA ACGAGGACAT AGCTGAGAAA CTTCAGTCTC CAGACGACGA AAGGAAGCA | 780 |
| ATCGTGACAG TGGAAGGAGG TCTCAGCGTT ATCAGCCCCA AGTGGCAAGA ACAACAAGA | 840 |
| GAAGATGAAG ATGAAGACGA AGATGATGAA GATGAACAAA TTCCCTCTCA CCCTCCTCG | 900 |
| CGACCAAGCC ATGGAAAGCG TGAACAAGAC GAGGACGAGG ACGAAGATGA AGATAAACC | 960 |
| CGTCCTAGTC GACCAAGCCA AGGAAAGCGT GAACAAGACC AGGACCAGGA CGAGGACG | 1020 |
| GATGAAGATG AAGATCAACC TCGCAAGAGC CGCGAATGGA GATCGAAAAA GACACAAC | 1080 |
| AGAAGACCTA GACAAGAAGA ACCACGTGAA AGAGGATGCG AGACAAGAAA CGGGGTTG | 1140 |
| GAAAATATCT GCACCTTGAA GCTTCACGAG AACATTGCTC GCCCTTCACG CGCTGACT | 1200 |
| TACAACCCTA AAGCTGGTCG CATTAGTACC CTCAACAGCC TCACCCTCCC AGCCCTCC | 1260 |
| CAATTCCAAC TCAGTGCCCA ATATGTTGTC CTCTACAAGA ATGGAATTTA CTCTCCAC | 1320 |

-continued

```
TGGAATCTGA ATGCAAACAG TGTGATCTAT GTGACTCGAG GACAAGGAAA GGTTAGAG      1380

GTGAACTGCC AAGGGAATGC AGTGTTCGAC GGTGAGCTTA GGAGGGGACA ATTGCTGG      1440

GTACCACAGA ACTTCGTGGT GGCGGAGCAA GCCGGAGAAC AAGGATTCGA ATACATAG      1500

TTCAAGACAC ACCACAACGC AGTCACTAGC TACTTGAAGG ATGTGTTTAG GGCAATTC      1560

TCAGAGGTTC TTGCCCATTC TTACAACCTT CGACAGAGTC AAGTGTCTGA GCTTAAGT      1620

GAAGGAAATT GGGGTCCTTT GGTCAACCCT GAGTCTCAAC AAGGCTCACC CCGTGTTA      1680

GTCGCATAA                                                              1689

(2) INFORMATION FOR SEQ ID NO: 15:

(i) SEQUENCE CHARACTERISTICS:
        (A) LENGTH: 1551 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

ATGGGGAAGC CCTTCTTCAC TCTCTCTCTT TCTTCCCTTT GCTTGCTACT CTTGTCGAGT       60

GCATGCTTTG CTATTACCTC CAGCAAGTTC AACGAGTGCC AACTCAACAA CCTCAACGC      120

TTGGAACCCG ACCACCGCGT TGAGTCCGAA GGTGGTCTTA TTGAAACATG GAACTCTCA      180

CACCCTGAGC TGCAATGCGC CGGTGTCACT GTTTCCAAAC GCACCCTCAA CCGCAACGG      240

TCCCACTTGC CATCTTACTT ACCTTATCCC CAAATGATCA TTGTCGTTCA AGGGAAGGG      300

GCAATTGGAT TTGCATTTCC GGGATGTCCC GAGACGTTTG AGAAGCCACA CAACAATC      360

AGCAGAAGAG GCTCAAGGTC ACAGCAGCAA CTACAAGACA GTCACCAGAA GATTCGTCA      420

TTCAATGAAG GAGACGTACT AGTGATTCCT CTTGGTGTTC CTTACTGGAC CTATAACAC      480

GGCGATGAAC CAGTTGTTGC CATCAGTCCT CTTGACACCT CCAACTTCAA CAATCAGCT      540

GATCAAAACC CCAGAGTATT TTACCTTGCT GGGAACCCAG ATATAGAGCA TCCCGAGAC      600

ATGCAACAAC AGCAGCAGCA GAAGAGTCAT GGTGGACGCA AGCAGGGGCA CACCGACA      660

CAGGAGGAAG AAGGTGGCAG TGTGCTCAGT GGCTTCAGCA ACATTTCTT AGCACAATC      720

TTCAACACCA ACGAGGACAC AGCTGAGAAA CTTCGGTCTC CAGATGACGA AAGGAAGCA      780

ATCGTGACAG TGGAGGGAGG CCTCAGCGTT ATCAGCCCCA AGTGGCAAGA ACAAGAAGA      840

GAAGACGAAG ACGAAGACGA AGAATATGGA CGGACGCCCT CTTATCCTCC ACGACGACC      900

AGCCATGGAA AGCATGAAGA TGACGAGGAC GAGGACGAAG AAGAAGATCA ACCTCGTCC      960

GATCACCCTC CACAGCGACC AAGCAGGCCC GAACAACAAG AACCACGTGG AAGAGGAT     1020

CAGACTAGAA ATGGGGTTGA GGAAAATATT TGCACCATGA AGCTTCACGA GAACATTG     1080

CGCCCTTCAC GTGCTGACTT CTACAACCCA AAAGCTGGTC GCATTAGCAC CCTCAACA     1140

CTCACCCTCC CAGCCCTCCG CCAATTCGGA CTCAGTGCCC AATATGTTGT CCTCTACA     1200

AATGGAATTT ACTCTCCAGA TTGGAACTTG AACGCGAACA GTGTGACGAT GACTCGAG     1260

AAAGGAAGAG TTAGAGTGGT GAACTGCCAA GGGAATGCAG TGTTCGACGG TGAGCTAA     1320

AGGGGACAAT TGCTAGTGGT GCCGCAGAAC CCCGCGGTGG CTGAGCAAGG GGGAGAAC     1380

GGATTGGAAT ATGTAGTGTT CAAGACACAC CACAACGCCG TGAGCAGCTA CATTAAGG     1440

GTGTTTAGGG TAATCCCTTC GGAGGTTCTT TCCAATTCTT ACAACCTTGG CCAGAGTC     1500

GTGCGTCAGC TCAAGTATCA AGGAAACTCC GGCCCTTTGG TCAACCCATA A            1551
```

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
GCGGCCGCAT GGCCAAGCTA GTTTTTT                                          27
```

(2) INFORMATION FOR SEQ ID NO: 17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
GCGGCCGCTG GTGGCGTTTG TGA                                              23
```

(2) INFORMATION FOR SEQ ID NO: 18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
GCGGCCGCTC TTCTGAGACT CCT                                              23
```

(2) INFORMATION FOR SEQ ID NO: 19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
GCGGCCGCAT GCCCTTCACT CTCT                                             24
```

(2) INFORMATION FOR SEQ ID NO: 20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
GCGGCCGCTG GGAGGGTGAG GCTGTT                                           26
```

(2) INFORMATION FOR SEQ ID NO: 21:

(i) SEQUENCE CHARACTERISTICS:

```
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

GCGGCCGCTG AGCCTTGTTG AGAC                                              24
```